US012033760B2

(12) United States Patent
Jones

(10) Patent No.: US 12,033,760 B2
(45) Date of Patent: Jul. 9, 2024

(54) SYSTEM AND METHOD FOR DETERMINING A SET OF PRINCIPAL COMPONENTS IN A MULTIVARIATE MEDICAL DATA

(71) Applicant: Mayo Foundation for Medical Education and Research, Rochester, MN (US)

(72) Inventor: David T. Jones, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 727 days.

(21) Appl. No.: 17/254,542

(22) PCT Filed: Jul. 1, 2019

(86) PCT No.: PCT/US2019/040191
§ 371 (c)(1),
(2) Date: Dec. 21, 2020

(87) PCT Pub. No.: WO2020/010022
PCT Pub. Date: Jan. 9, 2020

(65) Prior Publication Data
US 2021/0272701 A1 Sep. 2, 2021

Related U.S. Application Data

(60) Provisional application No. 62/693,267, filed on Jul. 2, 2018.

(51) Int. Cl.
*G16H 30/40* (2018.01)
*G06T 7/00* (2017.01)
(Continued)

(52) U.S. Cl.
CPC ........... *G16H 50/70* (2018.01); *G06T 7/0012* (2013.01); *G16H 10/40* (2018.01); *G16H 10/60* (2018.01);
(Continued)

(58) Field of Classification Search
CPC ..................................... A61B 5/4064
See application file for complete search history.

(56) References Cited

U.S. PATENT DOCUMENTS

| 11,263,749 B1* | 3/2022 | Purushottam .......... G16H 15/00 |
| 2006/0074290 A1* | 4/2006 | Chen ........................ G06T 7/97 |
| | | 600/407 |

(Continued)

FOREIGN PATENT DOCUMENTS

| WO | 2017011746 A1 | 1/2017 |
| WO | 2006 | 9/2019 |
| WO | 2020010022 A1 | 1/2020 |

OTHER PUBLICATIONS

Asim et al., "A multi-modal, multi-atlas-based approach for Alzheimer detection via machine learning", Research Article, Int J. Imaging System Technology, 2018, 1-11, Wiley Periodicals, Inc.
(Continued)

*Primary Examiner* — Jonathan Ng
(74) *Attorney, Agent, or Firm* — Daniel J. Chalker; Edwin S. Flores; Chalker Flores, LLP

(57) ABSTRACT

An apparatus and computerized method for determining a set of principal components in a multivariate medical data corresponding to a group of subjects comprises: providing a computing device comprising an input/output interface, a memory and one or more processors communicably coupled to the input/output interface and the memory; receiving the multivariate medical data via the input/output interface or the memory; identifying a set of variables based on metabolic patterns between the subjects in the multivariate data
(Continued)

using the one or more processors; representing the multivariate medical data corresponding to the set of variables in a high dimensional space between the subjects using the one or more processors; determining the set of principal components by reducing the high dimensional space between the subjects to a compact representational space using the one or more processors; and providing the set of principal components via the input/output interfaces.

20 Claims, 18 Drawing Sheets

(51) Int. Cl.
| | | |
|---|---|---|
| *G16H 10/40* | (2018.01) | |
| *G16H 10/60* | (2018.01) | |
| *G16H 30/20* | (2018.01) | |
| *G16H 40/67* | (2018.01) | |
| *G16H 50/20* | (2018.01) | |
| *G16H 50/70* | (2018.01) | |
| *G16H 70/60* | (2018.01) | |
| G16H 10/20 | (2018.01) | |
| G16H 20/10 | (2018.01) | |
| G16H 40/20 | (2018.01) | |

(52) U.S. Cl.
CPC .............. *G16H 30/20* (2018.01); *G16H 30/40* (2018.01); *G16H 40/67* (2018.01); *G16H 50/20* (2018.01); *G16H 70/60* (2018.01); *G06T 2207/10104* (2013.01); *G06T 2207/30016* (2013.01); *G16H 10/20* (2018.01); *G16H 20/10* (2018.01); *G16H 40/20* (2018.01)

(56) References Cited

U.S. PATENT DOCUMENTS

| | | | | |
|---|---|---|---|---|
| 2014/0350380 | A1* | 11/2014 | Eidelberg | A61B 5/055 600/436 |
| 2016/0300352 | A1* | 10/2016 | Raj | G06V 10/764 |
| 2018/0204327 | A1* | 7/2018 | Matthews | A61B 5/7275 |

OTHER PUBLICATIONS

Botha et al., "FDG-PET in tau-negative amnestic dementia resembles that of autopsy-proven hippocampal sclerosis", Brain, a Journal of Neurology, 2018:141;1201-1217.
Graff-Radford et al., "Dementia with Lewy bodies—Basis of cingulate island sign", 2014, American Academy of Neurology.
Jack Jr., et al., "NIA-AA Research Framework: Toward a biological Definition of Alzheimer's Disease", HHS Public Access, Alzheimers Dement, 2018, Apr. 14(4): 535-562.
Jones et al., "Cascading network failure across the Alzheimer's disease spectrum", Brain, A Journal o Neurology, 2016, 139; 547-562.
Jones et al., "Tau, Amyloid, and Cascading Network Failure Across the Alzheimer's Disease Spectrum", Cortex, Dec. 2017, 97:143-159.
Margulies et al., "Situating the Default-Mode Network Along a Principal Gradient of Macroscale Cortical Organization", PNAS, Nov. 2016, vol. 113, No. 44.
Shine et al., "Human Cognition Involves the Dynamic Integration f Neural Activity and Neuromodulatory Systems", Nature Neuroscience, Corrected: Publisher Correction, VOol 22, 2019, 289-296.
Shine et al., "Author Correction: Perceptual Straightening of Natural Videos", Published on Line: May 15, 2019.
Singh et al., "Deep Learning Based Classification of FDG-PET Data for Alzheimers Disease Categories", Proc SPIE Int Int Soc Opt Eng., Oct. 2017, 10572, Author Manuscript.
Townley et al., "18-F-FDG PET-CT Pattern in Idiopathic Normal Pressure Hydrocephalus", NeuroImage: Clinical, 18, 2018, 897-902.
Turk et al., "Eigenfaces for Recognition", Journal o Cognitive Neuroscience, vol. 3, No. 1.

* cited by examiner

| Variable | PC1 | PC2 | PC3 | PC4 | PC5 | F-statistic | P-value | adj R² |
|---|---|---|---|---|---|---|---|---|
| $FDG_{AD}$ | 0.7492 | -0.2981 | -0.3626 | -0.1894 | -0.0557 | $F_{(5,417)}=384$ | 2.20E-16 | 0.8194 |
| Age Onset | 0.0406 | -0.6186 | -0.2929 | -0.3144 | -0.154 | $F_{(5,350)}=100.6$ | 2.20E-16 | 0.5839 |
| $FDG_{TDP}$ | 0.4048 | -0.5288 | -0.137 | -0.2785 | 0.08556 | $F_{(5,417)}=100.8$ | 2.20E-16 | 0.5419 |
| $MRI_{AD}$ | 0.4964 | 0.04699 | -0.4365 | 0.03649 | -0.1997 | $F_{(5,411)}=76.07$ | 2.20E-16 | 0.4743 |
| MMSE | 0.4399 | -0.1832 | -0.4474 | -0.1607 | -0.0935 | $F_{(5,397)}=66.27$ | 2.20E-16 | 0.4481 |
| CDR-SOB | -0.442 | 0.14207 | 0.3791 | 0.1658 | 0.09993 | $F_{(5,417)}=55.02$ | 2.20E-16 | 0.3903 |
| Tau-PET | -0.058 | 0.27857 | 0.4275 | 0.26385 | 0.26644 | $F_{(5,132)}=17.57$ | 2.57E-13 | 0.3769 |
| HV | 0.3363 | 0.36584 | -0.1991 | 0.17241 | -0.1917 | $F_{(5,411)}=43.65$ | 2.20E-16 | 0.3389 |
| NFT | 0.007 | -0.0456 | 0.3246 | 0.09307 | 0.4 | $F_{(5,60)}=4.602$ | 0.001279 | 0.217 |
| Global-Z | 0.4518 | -0.0623 | -0.3345 | -0.0179 | -0.1004 | $F_{(5,160)}=9.821$ | 3.34E-08 | 0.2109 |
| Lewy Path | -0.312 | 0.35109 | 0.0049 | -0.0126 | 0.09469 | $F_{(5,58)}=3.836$ | 0.004528 | 0.1837 |
| High Tau | 0.0093 | -0.0522 | 0.2794 | 0.12364 | 0.31465 | $F_{(5,197)}=9.355$ | 5.16E-08 | 0.1714 |
| UPDRS | -0.223 | 0.14998 | -0.0985 | 0.07303 | -0.2186 | $F_{(5,401)}=12.48$ | 2.85E-11 | 0.1239 |
| RBD | -0.21 | 0.22046 | -0.1079 | 0.05099 | -0.0665 | $F_{(5,240)}=7.89$ | 6.73E-07 | 0.1233 |
| $FDG_{DLB}$ | 0.0262 | 0.2896 | -0.1804 | 0.07708 | -0.0535 | $F_{(5,417)}=12.03$ | 6.75E-11 | 0.1156 |
| Amyloid-PET | -0.167 | -0.1095 | 0.17 | -0.1709 | 0.16549 | $F_{(5,417)}=11.98$ | 7.58E-11 | 0.1151 |
| E4 | -0.0239 | -0.0211 | 0.0773 | 0.10876 | 0.22062 | $F_{(5,388)}=5.581$ | 5.57E-05 | 0.05508 |

$FDG_{AD}$ – FDG SUVR in AD signature regions; $FDG_{TDP}$ – FDG ratio 83% accurate in predicting presence of TDP-43 pathology; $MRI_{AD}$ – cortical thickness in AD signature regions; MMSE – Mini-Mental Status Exam; CDR-SOB – Clinical Dementia Rating Scale Sum of Boxes; HV – Hippocampal volume; NFT – Braak NFT stage; Global-Z – standardized global cognitive score; Lewy Path – Lewy Body Pathology; High Tau – either Braak NFT > IV-VI or Tau-PET SUVR > 1.33; UPDRS – Unified PD rating scale; RBD – REM Sleep Behavior Disorder; $FDG_{DLB}$ – cingulate island sign; E4 – presence of APOE ε4 allele

FIG. 1

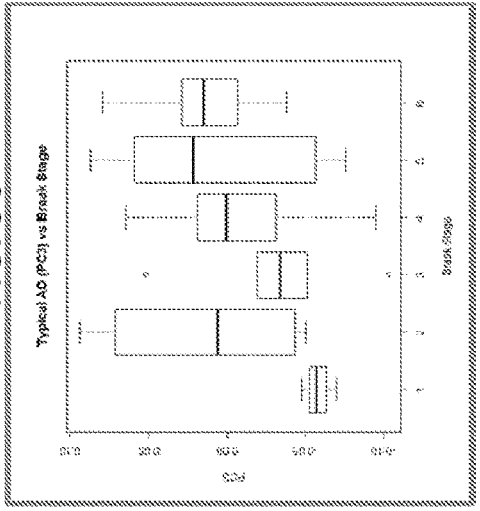
FIG. 3C
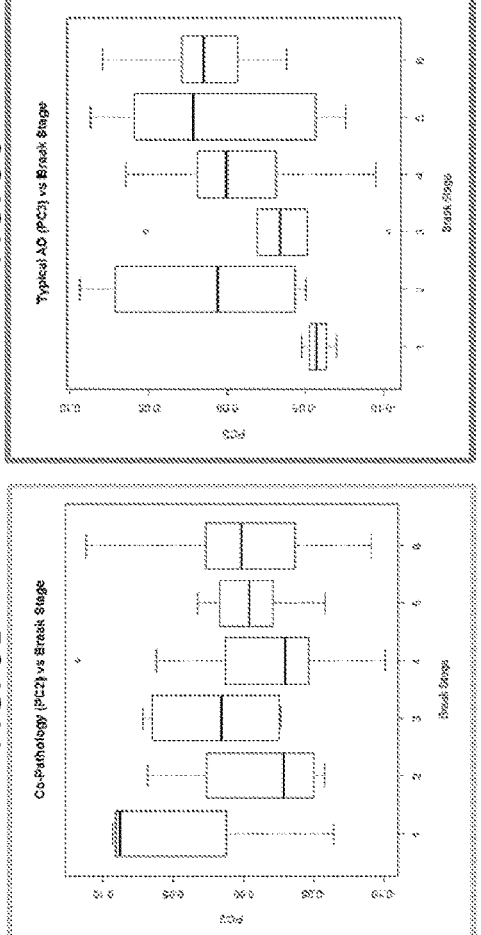
FIG. 3B
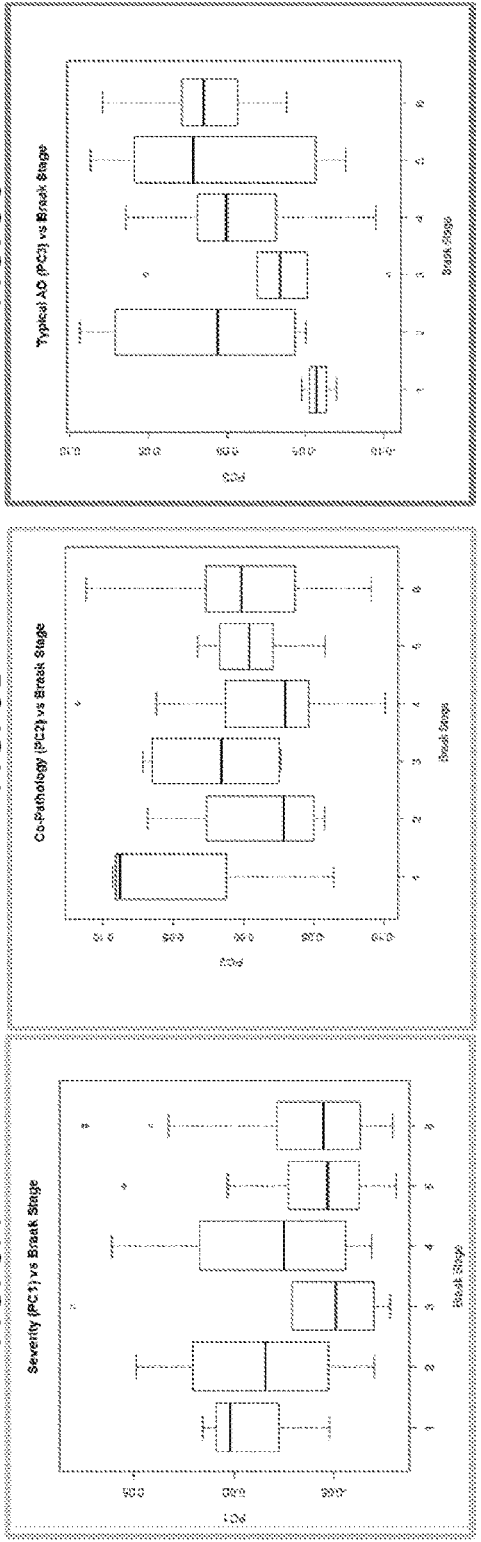
FIG. 3A
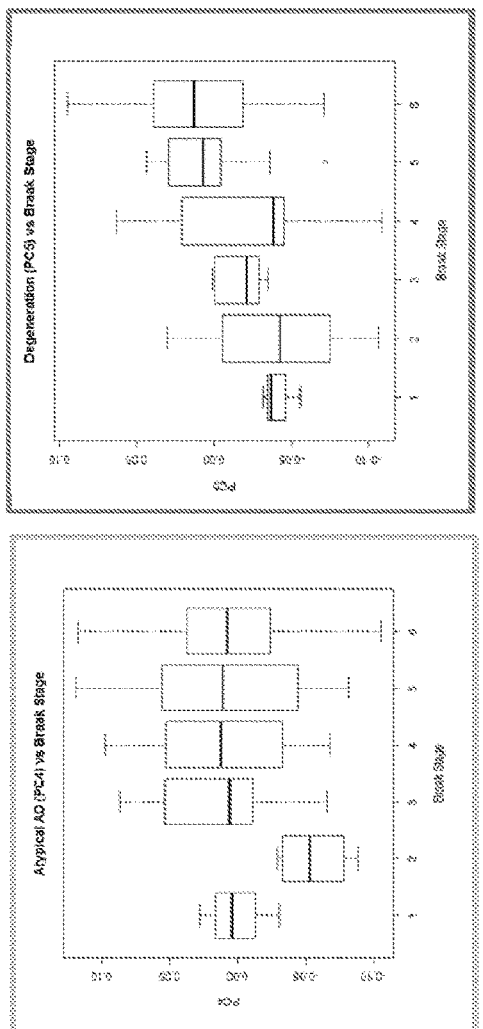
FIG. 3E
FIG. 3D
FIG. 3F

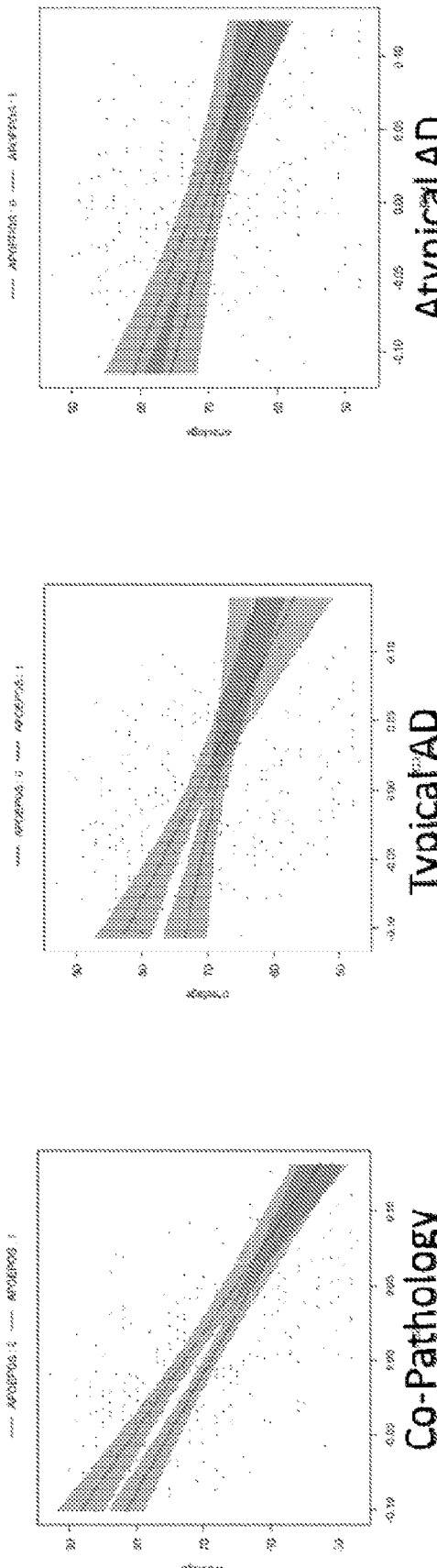
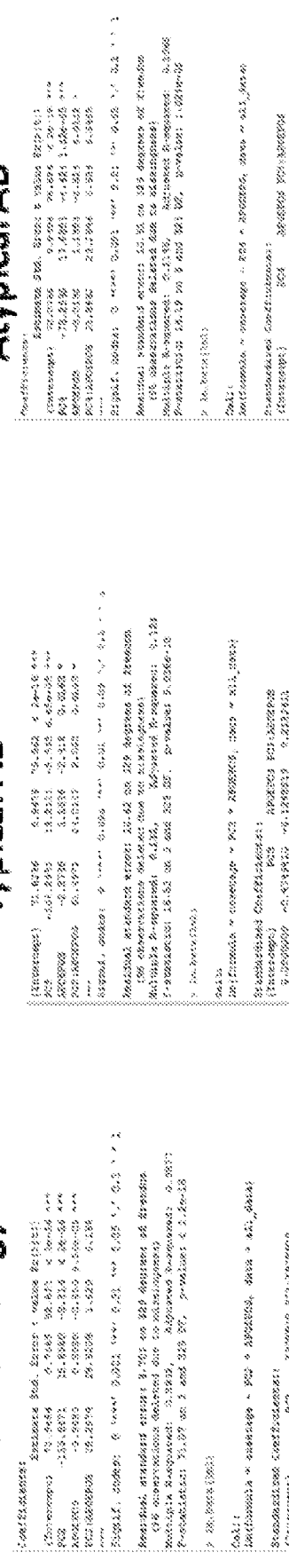
FIG. 4A
FIG. 4B
FIG. 4C
FIG. 4D

| Variable | PC1 | PC2 | PC3 | PC4 | PC5 | F-statistic | P-value | adjR² |
|---|---|---|---|---|---|---|---|---|
| FDG_TDP | 0.4048 | -0.5288 | -0.137 | -0.02785 | 0.08556 | F(5,417) = 100.8 | 2.20E-16 | 0.5419 |

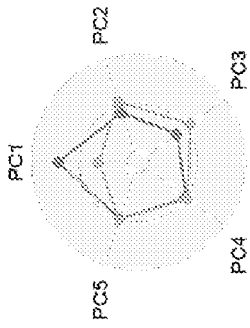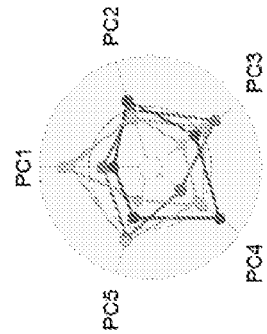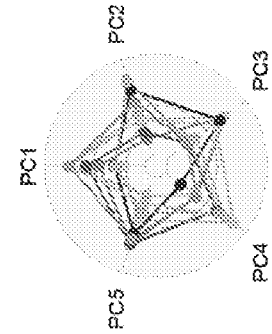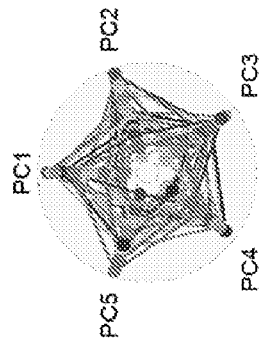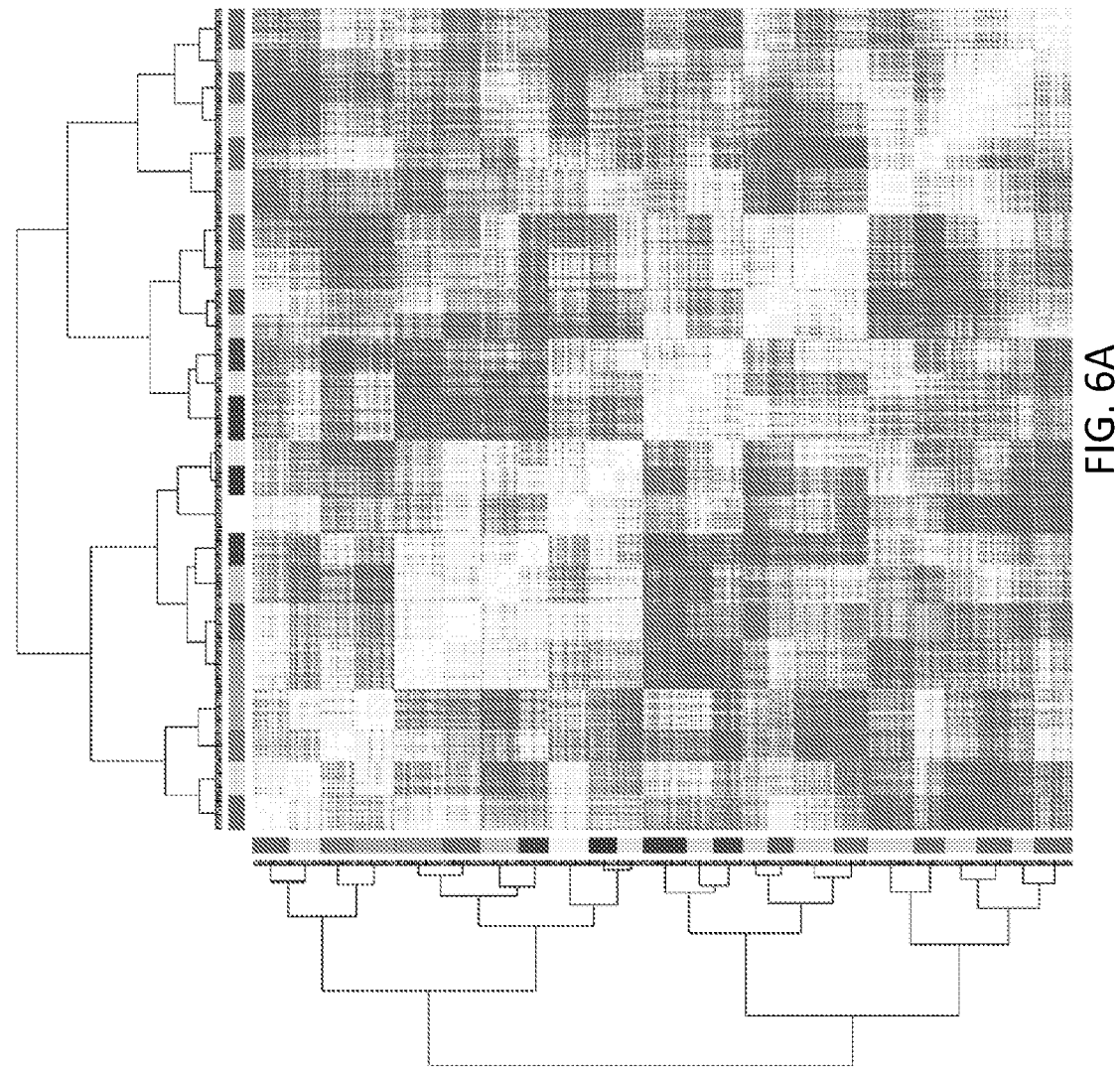

FIG. 10

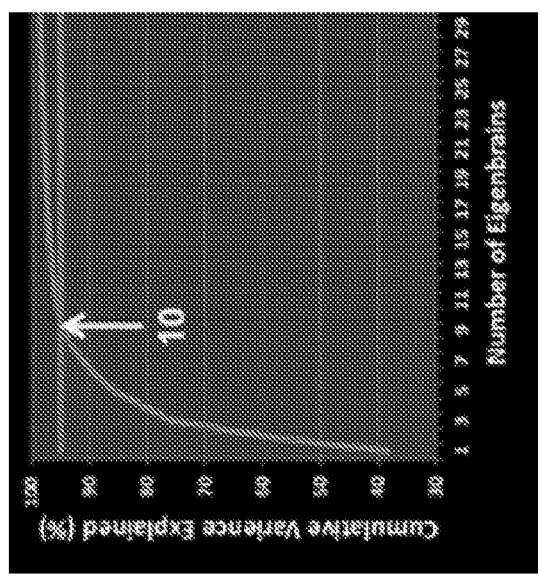
FIG. 15
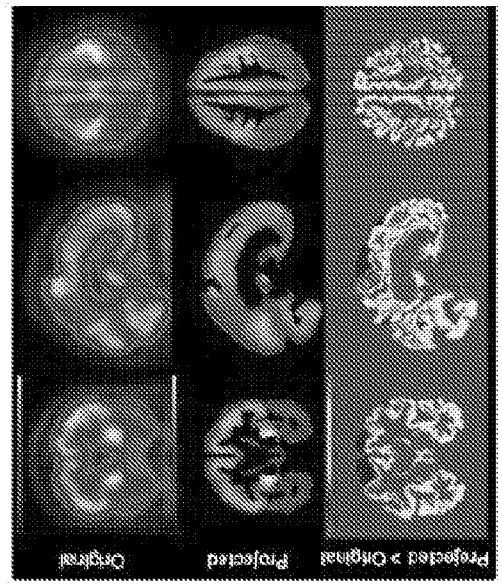
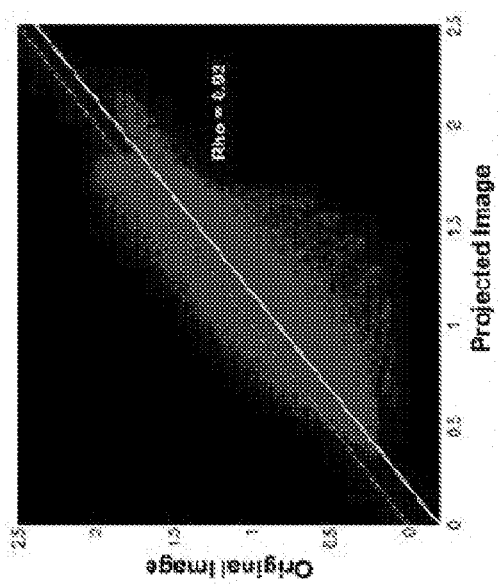
FIG. 16

SYSTEM AND METHOD FOR DETERMINING A SET OF PRINCIPAL COMPONENTS IN A MULTIVARIATE MEDICAL DATA

CROSS-REFERENCE TO RELATED APPLICATIONS

This application claims priority to and is a National Stage of International Application No. PCT/US2019/040191 filed on Jul. 1, 2019, which claims priority to U.S. Provisional Patent Application Ser. No. 62/693,267 filed on Jul. 2, 2018, both of which are hereby incorporated by reference in their entirety.

TECHNICAL FIELD OF THE INVENTION

The present invention relates in general to patient classification, and more particularly, to a system and method for determining a set of principal components in a multivariate medical data.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with Alzheimer's disease.

Understanding individual differences in patients usually begins with a clinician assigning a specific diagnosis to an individual and managing that individual using what is known about that diagnosis in other individuals. However there are well known inaccuracies in physician generated labels, or diagnosis.

For example, several clinical phenotypes of Alzheimer's disease (AD) are recognized, but there is substantial heterogeneity of clinical features within these recognized phenotypes and many individuals have features that overlap with two or more phenotypes. FDG-PET is a widely used objective clinical tool that is sensitive to phenotypic variability.

More specifically, there are biological and non-biological sources of variability in C-11 PiB scans. Efforts have been made to reduce the effects of non-biological sources of variability. However, subject related biological variability, beyond what can be attributed to beta-amyloid load, has not been routinely explored. Recently described variability in white matter binding [1] may confound methods of calculating standard uptake value ratios (SUVR) whether via explicit use of white matter ROIs or via partial volume averaging.

SUMMARY OF THE INVENTION

The present invention provides technology that uses multivariate medical data to determine a set of principal components. With large amounts of data, unsupervised machine learning algorithms can learn previously unseen features in the data that can be used to characterize individuals and their disease processes. Between-subject variance Projection and Reduction (BPR) is a novel unsupervised machine-learning algorithm which is based on a dimensionality reduction (e.g., PCA) of a high dimensionality representation of individual differences in multivariate patient data (e.g. voxels in an image or scores on a battery of clinical test, etc.). The reduced information represents machine intelligence that allows for a greater understanding of the individuals and the disease processes being measured. Single subject level phenotyping during life will allow for individualized clinical counseling and management.

For example, such phenotyping will advance the understanding of Alzheimer's disease (AD) pathophysiology and allow for improved clinical trial designs. A data-driven unsupervised machine learning algorithm uses patterns of neurodegeneration in FDG-PET to determine phenotypic classes in AD. This analysis helps to understand and isolate sources of variability encountered in PiB scanning of a large community dwelling sample of cognitively normal subjects.

In one embodiment, a computerized method for determining a set of principal components in a multivariate medical data corresponding to a group of subjects comprises: providing a computing device comprising an input/output interface, a memory and one or more processors communicably coupled to the input/output interface and the memory; receiving the multivariate medical data via the input/output interface or the memory; identifying a set of variables based on metabolic patterns between the subjects in the multivariate data using the one or more processors; representing the multivariate medical data corresponding to the set of variables in a high dimensional space between the subjects using the one or more processors; determining the set of principal components by reducing the high dimensional space between the subjects to a compact representational space using the one or more processors; and providing the set of principal components via the input/output interfaces. Moreover, the method can be implemented using a non-transitory computer readable medium that when executed causes the one or more processors to perform the method.

In one aspect, the method further comprises selecting the multivariate medical data for the group of subjects based on one or more medical observations. In another aspect, the multivariate medical data comprises an image data, a clinical test result, an individual characteristic or a combination thereof for each of the subjects. In another aspect, the method further comprises pre-processing the multivariate data. In another aspect, the multivariate data includes imaging data, and identifying the set of variables based on metabolic patterns between the subjects in the multivariate data using the one or more processors comprises: three-dimensional standard space ordering of FDG-PET voxels in the imaging data; creating a mask by one-dimensional ordering of the FDG-PET voxels that are in gray matter voxels; voxel-wise standardization of the FDG-PET voxels across all subjects using the mask; and identifying one or more of the set of variables using the voxel-wise standardization of the FDG-PET voxels. In another aspect, determining the set of principal components by reducing the high dimensional space between the subjects to a compact representational space is performed using a principal component analysis (PCA), a non-negative matrix factorization (NMF), a linear discriminant analysis (LDA), a generalized discriminant analysis (GDA), or a canonical correlation analysis (CCA). In another aspect, the method further comprises clustering the subjects into one or more groups based on at least one of the principal components. In another aspect, the method further comprises clustering the subjects into one or more phenotypes based on at least one of the principal components. In another aspect, the method further comprises characterizing the subjects and a disease process based on at least one of the principal components. In another aspect, the set of principal components explain a specified percentage of the high dimensional space. In another aspect, the method further comprises: determining an association between the set of principal components and one or more imaging, clinical and pathologic variables; and providing the association via the input/output interface. In another aspect, the method further comprises: receiving a medical data for a new subject via the input/output interface; analyzing the medical data based on the set of principal components using the one or more processors; and providing a diagnosis or a recommendation based on the analyzed medical data via the input/output device. In another aspect, the recommendation comprises a selection or exclusion of a therapy, medication, diagnostic testing, clinical trial or referral for the new subject. In another aspect, the method further comprises automatically predicting a post-mortem pathology for the new subject. In another aspect, the input/output interface comprises a remote device, and the remote device is communicably coupled to the one or more processors via one or more networks. In another aspect, the computing device comprises a server computer, a workstation computer, a laptop computer, a mobile communications device, a personal data assistant, or a medical device.

In another embodiment, an apparatus for determining a set of principal components in a multivariate medical data corresponding to a group of subjects comprises: an input/output interface; a memory; and one or more processors communicably coupled to the input/output interface and the memory. The one or more processors receive the multivariate medical data via the input/output interface or the memory, identify a set of variables based on metabolic patterns between the subjects in the multivariate data, represent the multivariate medical data corresponding to the set of variables in a high dimensional space between the subjects, determine the set of principal components by reducing the high dimensional space between the subjects to a compact representational space, and provide the set of principal components via the input/output interfaces.

In one aspect, the one or more processors select the multivariate medical data for the group of subjects based on one or more medical observations. In another aspect, the multivariate medical data comprises an image data, a clinical test result, an individual characteristic or a combination thereof for each of the subjects. In another aspect, the one or more processors pre-process the multivariate data. In another aspect, the multivariate data includes imaging data, and the one or more processors identify the set of variables based on metabolic patterns between the subjects in the multivariate data by: three-dimensional standard space ordering of FDG-PET voxels in the imaging data; creating a mask by one-dimensional ordering of the FDG-PET voxels that are in gray matter voxels; voxel-wise standardization of the FDG-PET voxels across all subjects using the mask; and identifying one or more of the set of variables using the voxel-wise standardization of the FDG-PET voxels. In another aspect, the one or more processors determine the set of principal components by reducing the high dimensional space between the subjects to a compact representational space is performed using a principal component analysis (PCA), a non-negative matrix factorization (NMF), a linear discriminant analysis (LDA), a generalized discriminant analysis (GDA), or a canonical correlation analysis (CCA). In another aspect, the one or more processors cluster the subjects into one or more groups based on at least one of the principal components. In another aspect, the one or more processors cluster the subjects into one or more phenotypes based on at least one of the principal components. In another aspect, the one or more processors characterize the subjects and a disease process based on at least one of the principal components. In another aspect, the set of principal components explain a specified percentage of the high dimensional space. In another aspect, the one or more processors: determine an association between the set of principal components and one or more imaging, clinical and pathologic variables; and provide the association via the input/output interface. In another aspect, the one or more processors: receive a medical data for a new subject via the input/output interface; analyze the medical data based on the set of principal components; and provide a diagnosis or a recommendation based on the analyzed medical data via the input/output device. In another aspect, the recommendation comprises a selection or exclusion of a therapy, medication, diagnostic testing, clinical trial or referral for the new subject. In another aspect, the one or more processors automatically predict a post-mortem pathology for the new subject. In another aspect, the input/output interface comprises a remote device, and the remote device is communicably coupled to the one or more processors via one or more networks. In another aspect, the computing device comprises a server computer, a workstation computer, a laptop computer, a mobile communications device, a personal data assistant, or a medical device.

BRIEF DESCRIPTION OF THE DRAWINGS

For a more complete understanding of the features and advantages of the present invention, reference is now made to the detailed description of the invention along with the accompanying figures and in which:

FIG. 1 is a table illustrating that the five phenotypic axes had strong associations with Alzheimer's disease imaging, clinical, and pathologic variables tested in accordance with one embodiment of the present invention;

FIGS. 3A-3F illustrate the associations between the five phenotypic axes and Braak NFT stage in accordance with one embodiment of the present invention;

FIGS. 4A-4D illustrate the associations between the phenotypic axes and age onset in accordance with one embodiment of the present invention;

FIGS. 6A-6E illustrates high dimensional representation and clustering of between subject similarities in accordance with one embodiment of the present invention;

FIG. 10 is a table illustrating the data associated with the various variables in accordance with one embodiment of the present invention;

FIG. 15 is a graph showing the cumulative percentage of variance explained for the first 30 eigenbrains in accordance with one embodiment of the present invention;

FIG. 16 depicts an Eigenbrain based reconstruction of one subject in accordance with one embodiment of the present invention;

DETAILED DESCRIPTION OF THE INVENTION

Figure 2:
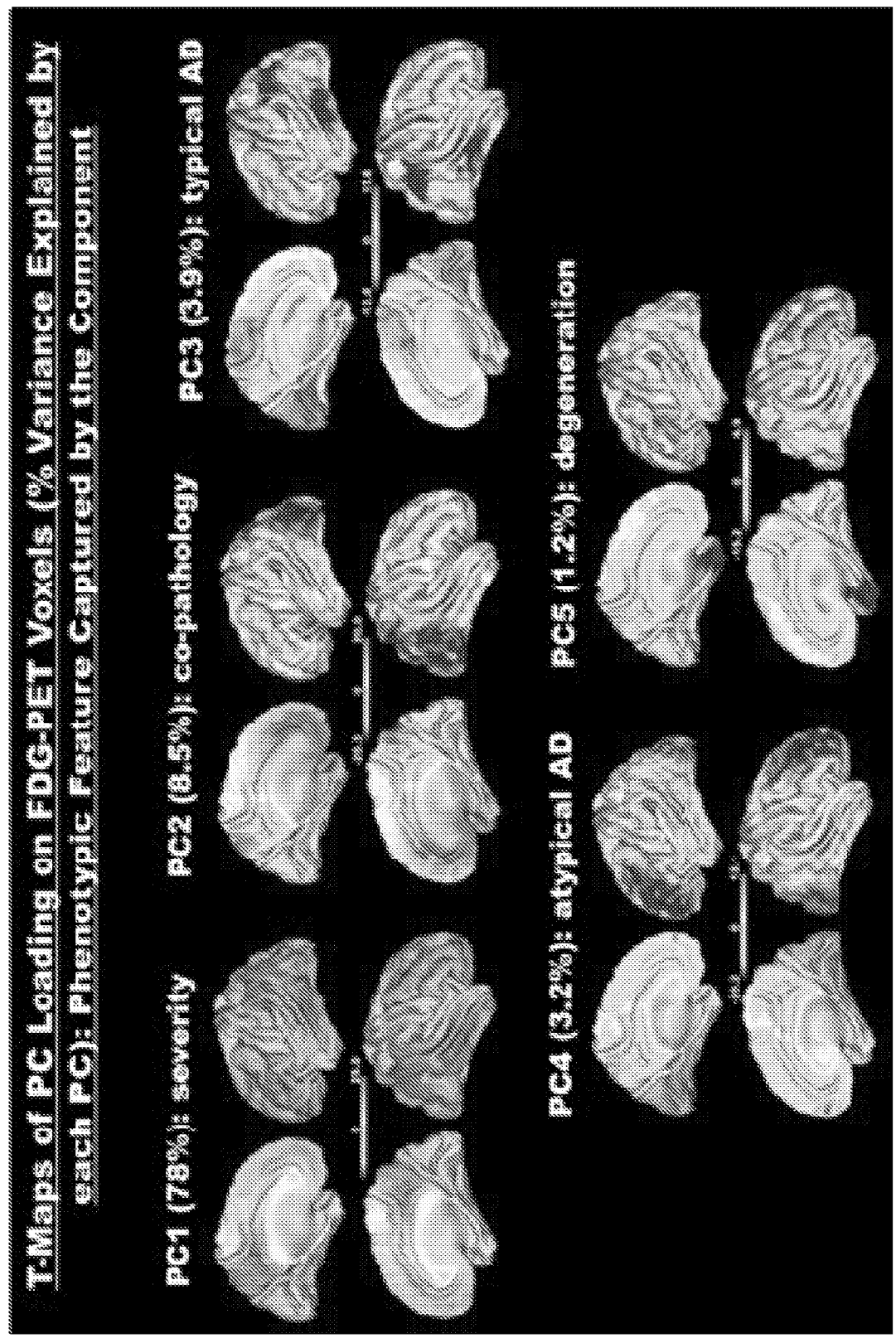
FIG. 2 illustrates the spatial loading of the axes in FDG space in accordance with one embodiment of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention provides technology that uses multivariate medical data to determine a set of principal components. With large amounts of data, unsupervised machine learning algorithms can learn previously unseen features in the data that can be used to characterize individuals and their disease processes. Between-subject variance Projection and Reduction (BPR) is a novel unsupervised machine-learning algorithm which is based on a dimensionality reduction (e.g., PCA) of a high dimensionality representation of individual differences in multivariate patient data (e.g. voxels in an image or scores on a battery of clinical test, etc.). The reduced information represents machine intelligence that allows for a greater understanding of the individuals and the disease processes being measured. Single subject level phenotyping during life will allow for individualized clinical counseling and management.

For example, such phenotyping will advance the understanding of Alzheimer's disease (AD) pathophysiology and allow for improved clinical trial designs. A data-driven unsupervised machine learning algorithm uses patterns of neurodegeneration in FDG-PET to determine phenotypic classes in AD. This analysis helps to understand and isolate sources of variability encountered in PiB scanning of a large community dwelling sample of cognitively normal subjects.

A version of the algorithm was applied to FDG-PET imaging data from 423 individuals with AD dementia. The algorithm learned five principle features of AD (severity, co-pathology, typical AD, atypical AD, and neurodegeneration) that were used to cluster individuals into 13 distinct clinical phenotypes of AD with unique clinical trajectories.

All participants in the study that were PiB-PET positive (SUVR>1.5) and had CDR>0 that had FDG-PET were included (N=423); a subset (N=66) had post-mortem pathologic data available. All images underwent our novel unsupervised machine-learning algorithm, which is based on a dimensionality reduction (e.g., PCA) of a high dimensionality representation of individual differences in multivariate patterns of neurodegeneration evident on an imaging modality. Five principal components explained ~95% of the variability and were used to make clinical, imaging, and pathologic associations as well as exemplar-based agglomerative hierarchical clusters.

As shown in the table in FIG. 1, the five phenotypic axes had strong associations with imaging, clinical, and pathologic variables tested. The pathologic variables tested were: $FDGA_{AD}$—FDG SUVR in AD signature regions; $FDG_{TDP}$—FDG ratio 83% accurate in predicting presence of TDP-43 pathology; $MRI_{AD}$—cortical thickness in AD signature regions; MMSE—Mini-Mental Status Exam; CDR-SOB—Clinical Dementia Rating Scale Sum of Boxes; HV—Hippocampal volume; NFT—Braak NFT stage; Global-Z—standardized global cognitive score; Lewy Pathe—Lewy Body Pathology; High Tau—either Braak NFT>IV-VI or Tau-PET SUVR>1.33; UPDRS—Unified PD rating scale; RBD—REM Sleep Behavior Disorder; $FGD_{DLB}$—cingulate island sign; and E4—presence of APOE ε4 allele. The spatial loading of the axes in FDG space is displayed in FIG. 2. PC1 loaded on variables associated with severity (e.g., $FDG_{AD}$, CDR-SOB, cognitive scores, and neurodegenerative measures, but not with Braak NFT stage or Tau-PET). PC1 had a 78% variance explained by the PC. PC2 loaded onto age of disease onset and markers of co-pathology. PC2 had an 8.5% variance explained by the PC. PC3 loaded onto typical AD markers and Braak NFT stage. PC3 had a 3.9% variance explained by the PC. PC4 captured atypical AD features associated with frontal and posterior variants. PC4 had a 3.2% variance explained by the PC. PC5 loaded with markers of neurodegeneration and had the strongest association with Braak NFT stage. PC5 had a 1.2% variance explained by the PC.

FIGS. 3A-3F illustrate the associations between the phenotypic axes and Braak NFT stage. More specifically, FIG. 3A shows severity (PC1) versus Braak NFT stage. FIG. 3B shows co-pathology (PC2) versus Braak NFT stage. FIG. 3C shows typical AD (PC3) versus Braak NFT stage. FIG. 3D shows atypical AD (PC4) versus Braak NFT stage. FIG. 3E shows degeneration (PC5) versus Braak NFT stage. FIG. 3F shows Braak NFT stage data for the five phenotypic axes from FIG. 1.

FIGS. 4A-4D illustrate the associations between the phenotypic axes and age onset. More specifically, FIG. 4A shows co-pathology (PC2) versus onset age. FIG. 4B shows typical AD (PC3) versus onset age. FIG. 4C shows atypical AD (PC4) versus onset age. FIG. 4D shows onset age data for the five phenotypic axes from FIG. 1.

Figures 5A, 5B, 5C, 5D:
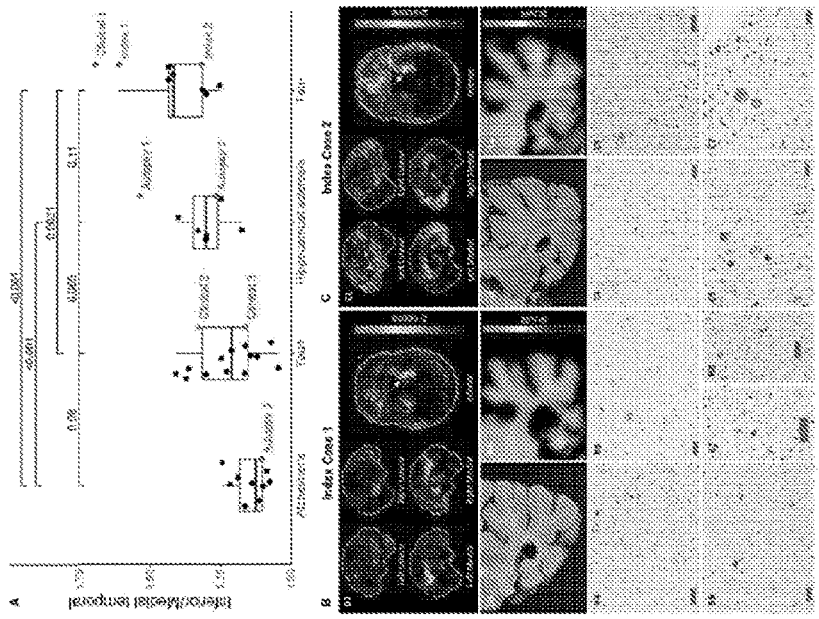
FIGS. 5A-5E illustrate the associations between the phenotypic axes and FDG in accordance with one embodiment of the present invention.
Figure 5E:
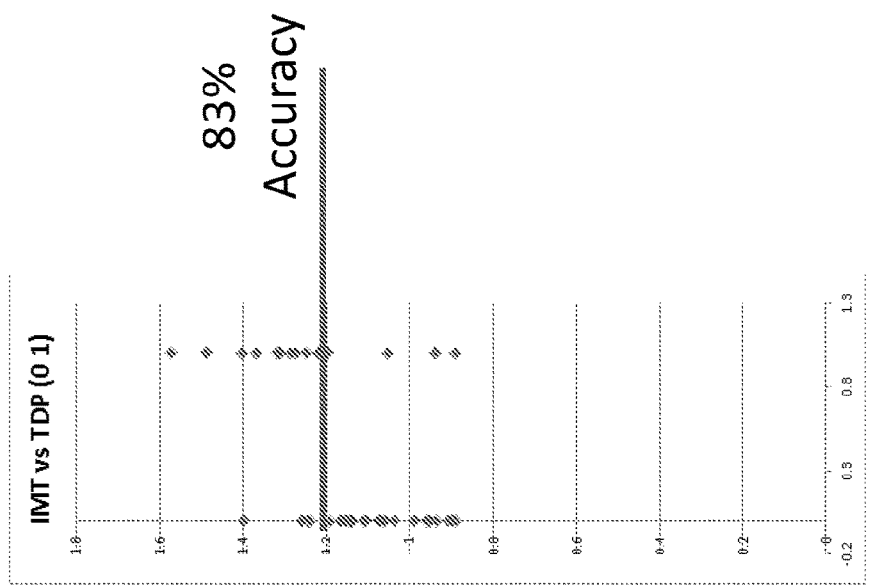

FIGS. 5A-5E illustrate the associations between the phenotypic axes and FDG. More specifically, FIG. 5A shows inferior/medial temporal versus TDP. FIG. 5B shows inferior/medial temporal versus Alzheimer's, Tau, hippocampal sclerosis and Tau. FIG. 5C shows FDG scans for index case 1. FIG. 5D shows FDG scans for index case 2. FIG. 5E shows onset age data for the five phenotypic axes from FIG. 1.

FIGS. 6A-6E illustrates high dimensional representation and clustering of between subject similarities. FIG. 6A shows a multidimensional graph of between subject similarities. FIG. 6B is a radial graph of the five phenotypic axes at the first (highest) cluster level. FIG. 6C is a radial graph of the five phenotypic axes at the second cluster level. FIG. 6C is a radial graph of the five phenotypic axes at the third cluster level. FIG. 6D is a radial graph of the five phenotypic axes at the fourth (lowest) cluster level.

Figure 7:
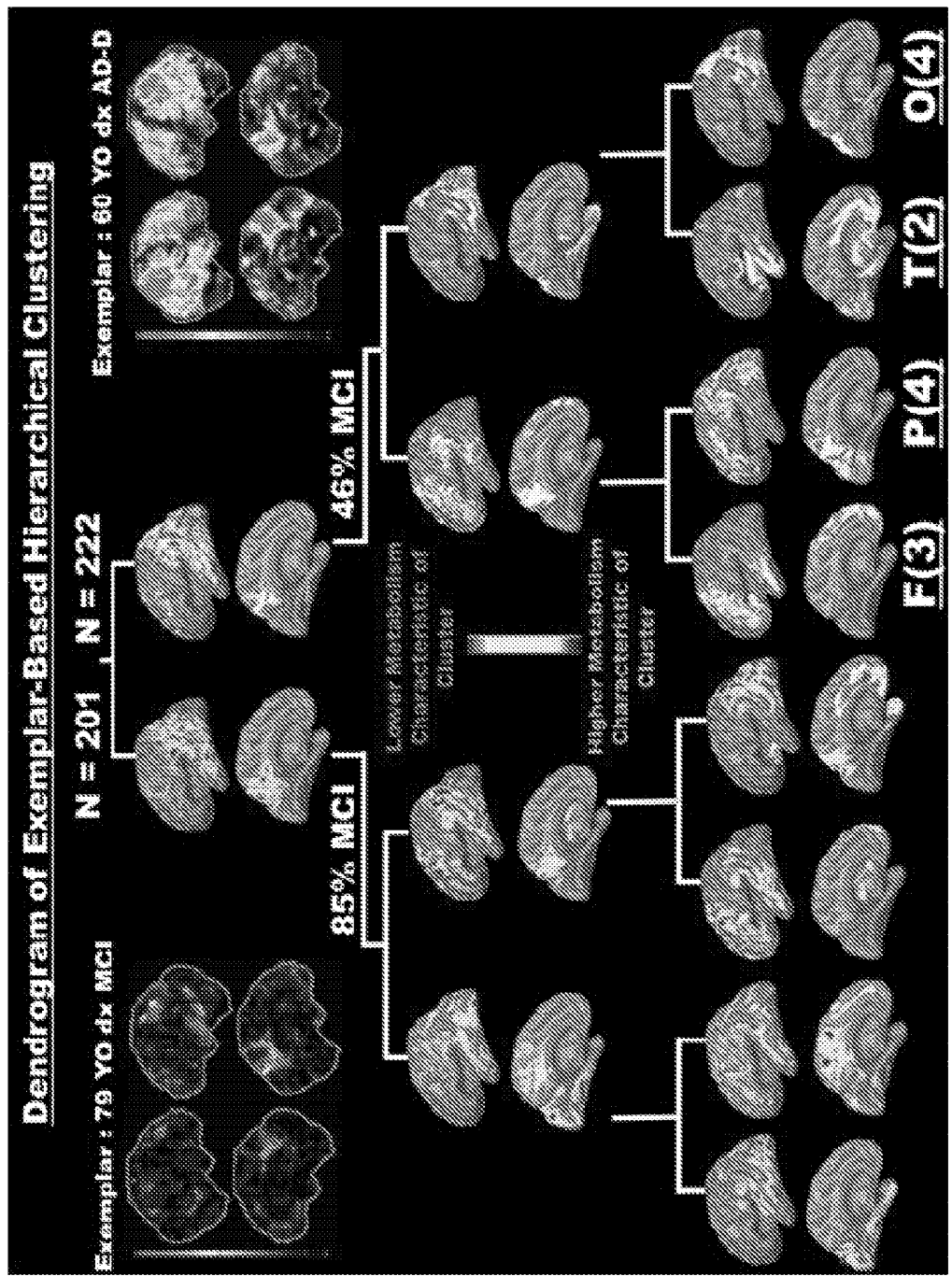
FIG. 7 illustrates dividing the groups in two using severity/PC1 in accordance with one embodiment of the present invention.

FIG. 7 shows the first three levels of the dendrogram of the agglomerative hierarchical clustering of the 423 subjects. At each level, the average characteristic metabolism for the group is projected on a medial and lateral surface rendering. The clustering or top binary split mainly divided the groups in two based on severity/PC1 with 85% of the subjects on the left having MCI versus only 46% in the right cluster. The CortexID images (GE Healthcare, Waukesha, WI, USA) of the exemplar for the top level is displayed in the upper left and right corners in order to view the representative participant level FDG-PET scans. These CortexID images are also used in FIG. 4 for the 13 AD dementia clusters at the lowest level of the clustering dendrogram.

Figure 8:
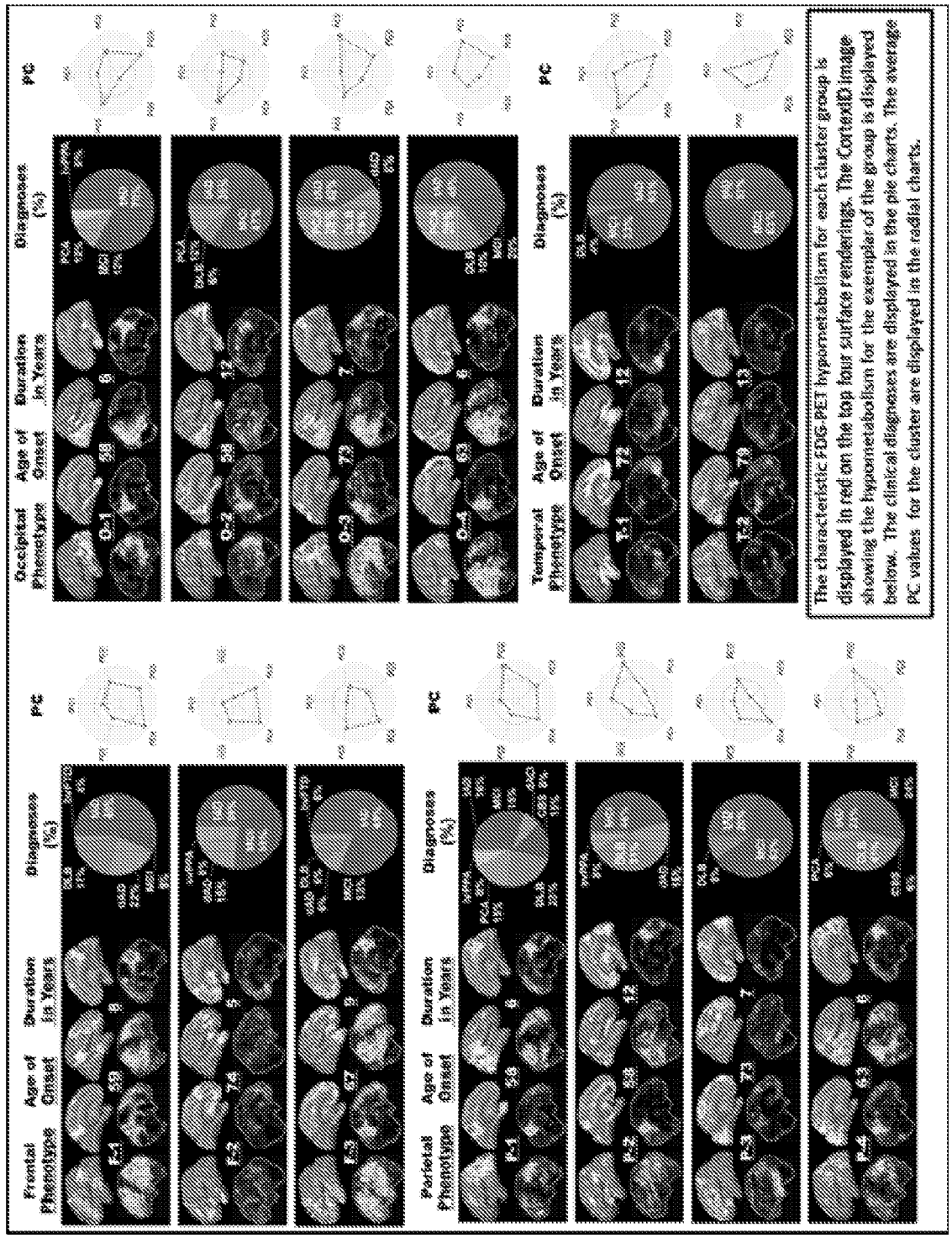
FIG. 8 illustrates clustering the dementia group into 13 phenotypes with unique clinical features.

As shown in FIG. 8, the dementia group clustered into 13 phenotypes with unique clinical features: 3 frontal, 4 parietal, 2 temporal, and 4 occipital. The characteristic FDG-PET hypometabolism for each cluster group is displayed in red on the top four surface renderings. The CortexID image showing the hypometabolism for the exemplar of the group is displayed below the surface renderings. The clinical diagnoses are displayed in the pie charts. The average PC values for the cluster are displayed in the radial charts.

These FDG-PET based AD-phenotypes advance the understanding of AD pathophysiology and may allow for individualized counseling and optimized clinical trial designs.

Figure 9:
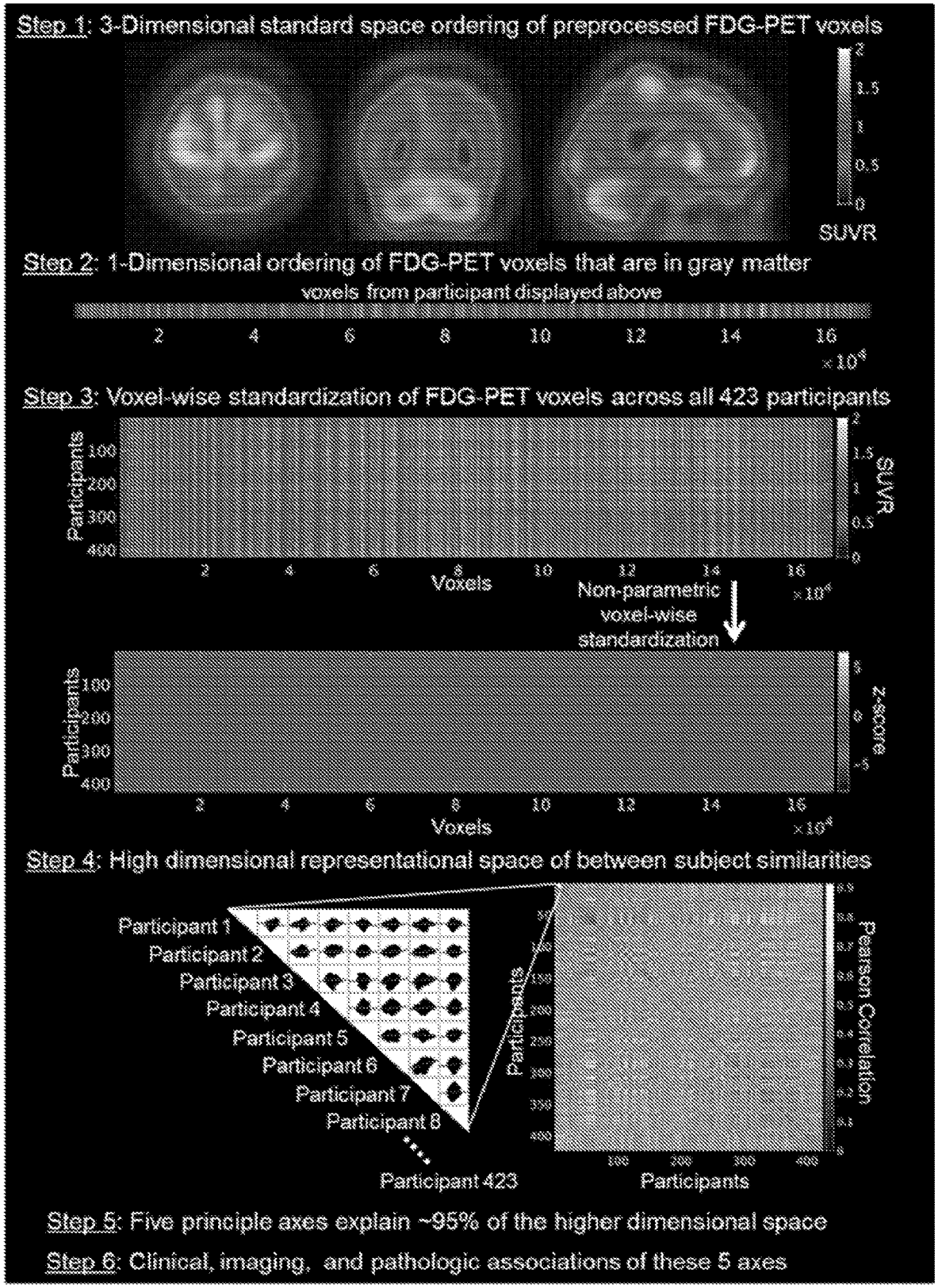
FIG. 9 illustrates the BPR procedure in accordance with one embodiment of the present invention.

The BPR procedure is: (1) B: Multivariate patterns available for a large amount of observations (e.g., subjects); (2) P: High-dimensional projection of between observations similarities; and (3) R: Reduction of the high-dimensional space to a compact representational space. FIG. 9 illustrates the BPR procedure with respect to the study described above:
Step 1: 3-Dimensional standard space ordering of preprocessed FDG-PET voxels;
Step 2: 1-Dimensional ordering of FDG-PET voxels that are in gray matter voxels from participant displayed above in Step 1;
Step 3: Voxel-wise standardization of FDG-PET voxels across all 423 participants;
Step 4: High dimensional representational space of between subject similarities;
Step 5: Five principle axes explain approximately 95% of the higher dimensional data; and
Step 6: Clinical, imaging, and pathologic associations of these five axes.

Figure 10:
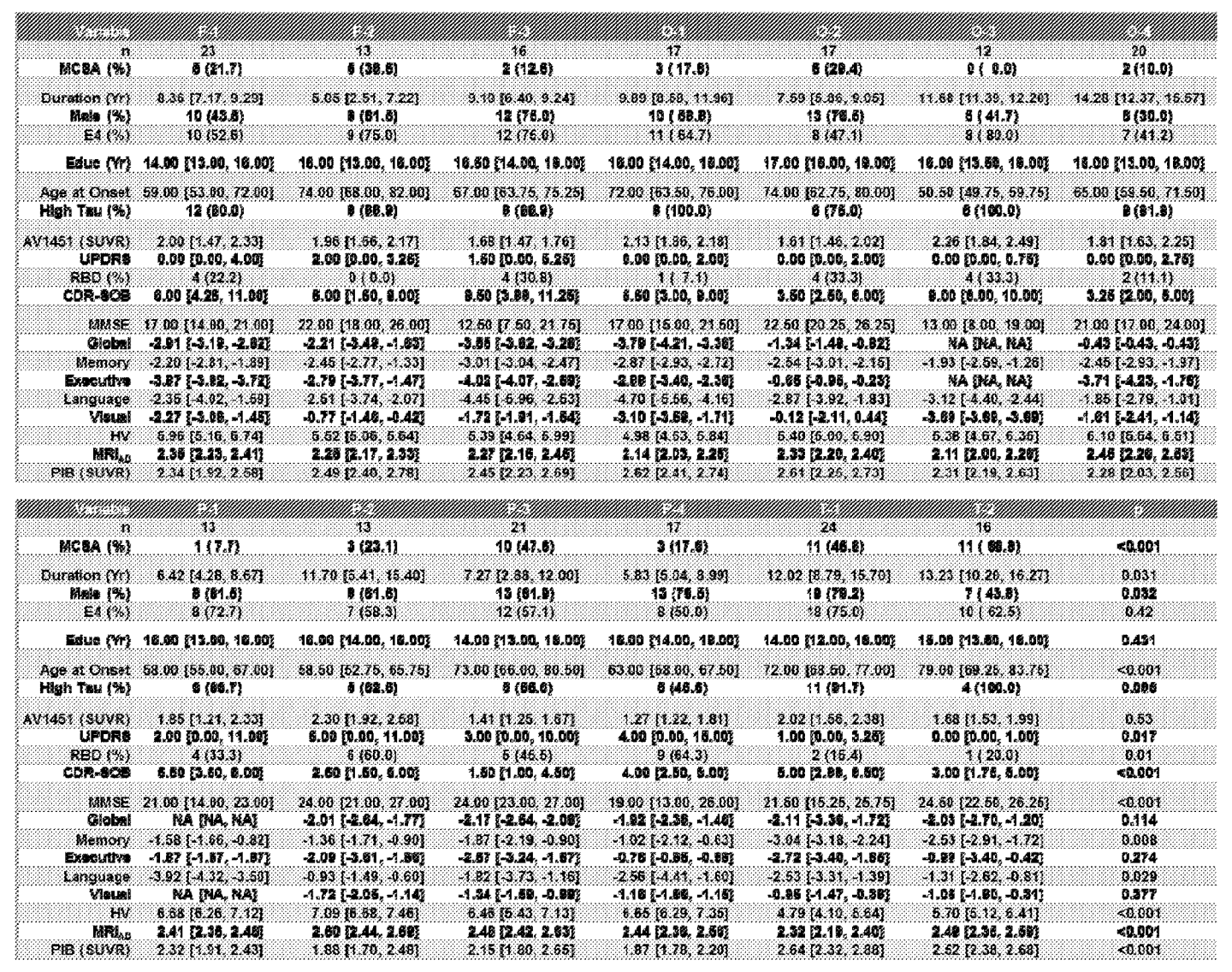

FIG. 10 is a table illustrating the data associated with the various variables in accordance with one embodiment of the present invention.

Although the foregoing non-limiting examples relate to Alzheimer's disease, the present invention can be used for determining a set of principal components in a multivariate medical data corresponding to a group of subjects as described below in reference to FIGS. 11-12.

In another example, BPR has been used in connection with maps of functional connectivity. Resting state fMRI were performed and maps of brain functional connectivity were computed. These functional connectivity maps are then subjected to the BPR procedure. The information learned by doing the BPR procedure on this data set relates to IQ and individual differences in personality. Knowing this information will be helpful in guiding individualized medicine relating to these individual differences. This will be especially relevant in managing neuropsychiatric disorders, pervasive developmental disorders, personality disorders, and improving inter-individual cooperation within groups by tailoring the group structure to the individual phenotypes comprising the group. The BPR procedure in this cohort was performed in a similar fashion as was done for FDG-PET scans. Thereafter, the learned information can be used to cluster subjects or characterized individual differences in IQ and personality.

The power and novelty of the BPR algorithm comes from the fact that the information learned is derived from the variability present in a high-dimensional projection of individual differences rather than in the variability present in the medical data itself or a projection of the variability in the data. This algorithm treats medical data from an individual as representing a particular parameterization of a (patho) physiological process of interest and uses individual differences in this parametrization to define a high dimensional state space. This high-dimensional state space, defined by individual variability rather than medical data variability, is then reduced to a low-dimensional space highly representative of the (patho)physiological process of interest. This low-dimensional representation can then be used to phenotype individual patients to guide therapeutic strategies, enrolment in clinical trials, prognostic counseling, and many other individualized medicine or precision medicine applications.

For example, one could obtain a multivariate data-point from the transcriptome profile from a patient's small-cell lung cancer biopsy combined with age, other demographics, and their metabolomics profile obtained from serum. This single multivariate data point would represent a particular parameterization of small-cell lung cancer in the context of this particular patient at this particular point in time. As long as this same data is obtained from large enough number of patients, then the parameter space of lung cancer will be able to be adequately sampled and a high-dimensional representational space can be constructed. This high dimensional space can then be reduced to a low-dimensional space representing the learned information about small-cell lung cancer. The low-dimensional coordinates can be estimated for any subject unseen by the original learning algorithm. The low-dimensional representation of a group of individuals can then be clustered into phenotypes which are now based on the pathophysiology of interest. For example, these profiles can then determine a particular therapy for an individual's small-cell lung cancer or enrollment in a clinical trial addressing that particular aspect of the pathophysiology of small-cell lung cancer. Given that this algorithm learns (patho)physiological information based on individual differences, it is very powerful at defining individual differences that can be used in precision medicine applications of all types.

Figure 11:
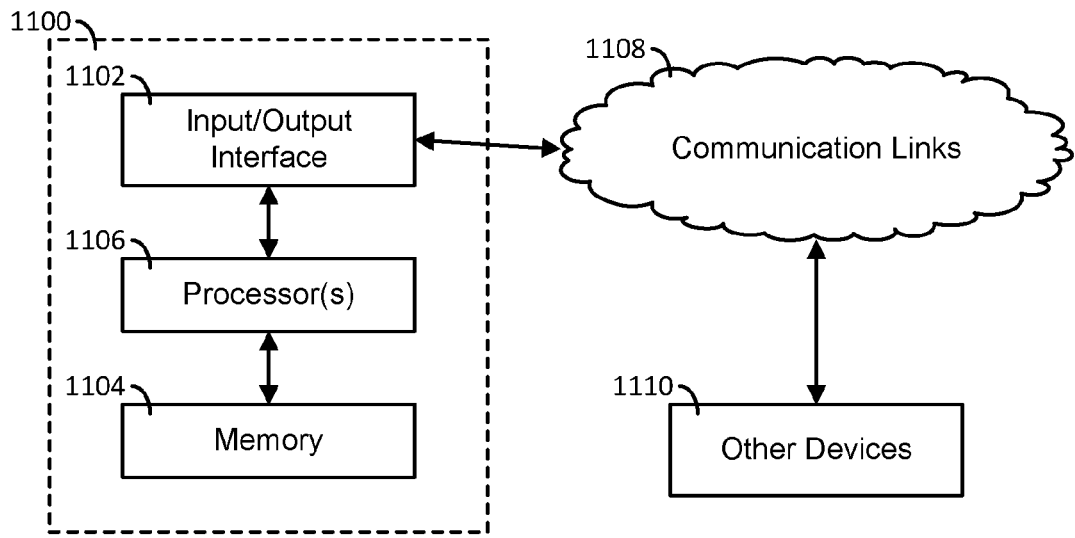
FIG. 11 is a block diagram of an apparatus in accordance with one embodiment of the present invention.

Now referring to FIG. 11, an apparatus 1100 for determining a set of principal components in a multivariate medical data corresponding to a group of subjects in accordance with one embodiment of the present invention is shown. The apparatus 1100 includes an input/output interface 1102, a memory 1102, and one or more processors 1106 communicably coupled to the input/output interface 1102 and the memory 1104. The one or more processors 1106 receive the multivariate medical data via the input/output interface 1102 or the memory 1104, identify a set of variables based on metabolic patterns between the subjects in the multivariate data, represent the multivariate medical data corresponding to the set of variables in a high dimensional space between the subjects, determine the set of principal components by reduce the high dimensional space between the subjects to a compact representational space, and provide the set of principal components via the input/output interfaces 1102.

In one aspect, the one or more processors 1106 select the multivariate medical data for the group of subjects based on one or more medical observations. In another aspect, the multivariate medical data comprises an image data, a clinical test result, an individual characteristic or a combination thereof for each of the subjects. In another aspect, the one or more processors 1106 pre-process the multivariate data. In another aspect, the multivariate data includes imaging data, and the one or more processors 1106 identify the set of variables based on metabolic patterns between the subjects in the multivariate data by: three-dimensional standard space ordering of FDG-PET voxels in the imaging data; creating a mask by one-dimensional ordering of the FDG-PET voxels that are in gray matter voxels; voxel-wise standardization of the FDG-PET voxels across all subjects using the mask; and identifying one or more of the set of variables using the voxel-wise standardization of the FDG-PET voxels. In another aspect, the one or more processors 1106 determine the set of principal components by reducing the high dimensional space between the subjects to a compact representational space is performed using a principal component analysis (PCA), a non-negative matrix factorization (NMF), a linear discriminant analysis (LDA), a generalized discriminant analysis (GDA), or a canonical correlation analysis (CCA). In another aspect, the one or more processors 1106 cluster the subjects into one or more groups based on at least one of the principal components. In another aspect, the one or more processors 1106 cluster the subjects into one or more phenotypes based on at least one of the principal components. In another aspect, the one or more processors 1106 characterize the subjects and a disease process based on at least one of the principal components. In another aspect, the set of principal components explain a specified percentage of the high dimensional space. In another aspect, the one or more processors 1106: determine an association between the set of principal components and one or more imaging, clinical and pathologic variables; and provide the association via the input/output interface 1102. In another aspect, the one or more processors 1106: receive a medical data for a new subject via the input/output interface 1102; analyze the medical data based on the set of principal components; and provide a diagnosis or a recommendation based on the analyzed medical data via the input/output device 1102. In another aspect, the recommendation comprises a selection or exclusion of a therapy, medication, diagnostic testing, clinical trial or referral for the new subject. In another aspect, the one or more processors 1106 automatically predict a post-mortem pathology for the new subject. In another aspect, the input/output interface 1102 comprises a remote device 1110, and the remote device 1110 is communicably coupled to the one or more processors 1106 via one or more networks 1108. In another aspect, the computing device 1100 comprises a server computer, a workstation computer, a laptop computer, a mobile communications device, a personal data assistant, or a medical device.

Figure 12:
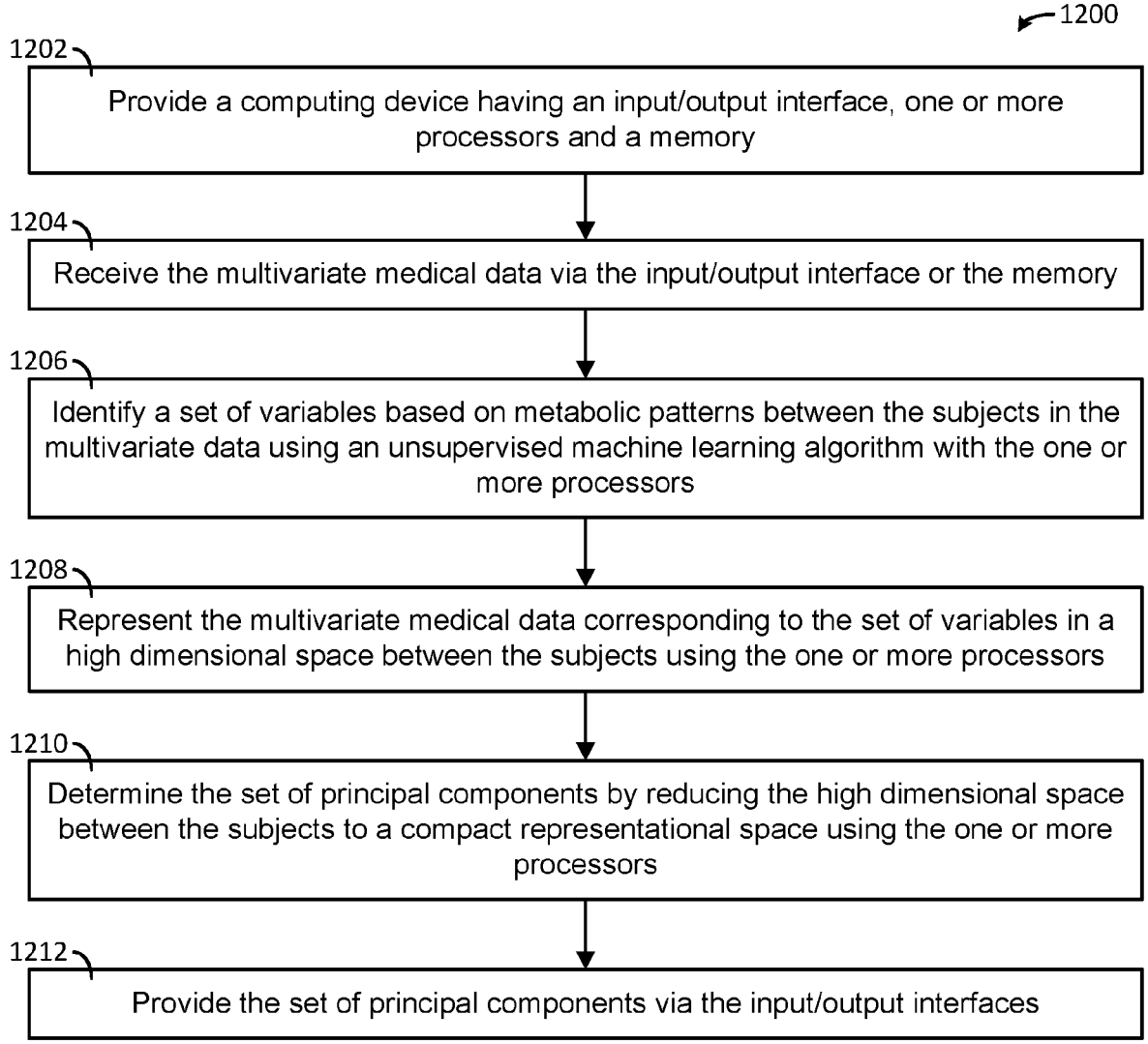
FIG. 12 is a flow chart of a method in accordance with one embodiment of the present invention.

Referring now to FIG. 12, a computerized method 1200 for determining a set of principal components in a multivariate medical data corresponding to a group of subjects in accordance with one embodiment of the present invention is shown. A computing device comprising an input/output interface, a memory and one or more processors communicably coupled to the input/output interface and the memory is provided in block 1202. The multivariate medical data is received via the input/output interface or the memory in block 1204. A set of variables is identified based on metabolic patterns between the subjects in the multivariate data using the one or more processors in block 1206. The multivariate medical data corresponding to the set of variables is represented in a high dimensional space between the subjects using the one or more processors in block 1208. The set of principal components is determined by reducing the high dimensional space between the subjects to a compact representational space using the one or more processors in block 1210. The set of principal components is provided via the input/output interfaces in block 1212. Moreover, the method can be implemented using a non-transitory computer readable medium that when executed causes the one or more processors to perform the method.

In one aspect, the method further comprises selecting the multivariate medical data for the group of subjects based on one or more medical observations. In another aspect, the multivariate medical data comprises an image data, a clinical test result, an individual characteristic or a combination thereof for each of the subjects. In another aspect, the method further comprises pre-processing the multivariate data. In another aspect, the multivariate data includes imaging data, and identifying the set of variables based on metabolic patterns between the subjects in the multivariate data using the one or more processors comprises: three-dimensional standard space ordering of FDG-PET voxels in the imaging data; creating a mask by one-dimensional ordering of the FDG-PET voxels that are in gray matter voxels; voxel-wise standardization of the FDG-PET voxels across all subjects using the mask; and identifying one or more of the set of variables using the voxel-wise standardization of the FDG-PET voxels. In another aspect, determining the set of principal components by reducing the high dimensional space between the subjects to a compact representational space is performed using a principal component analysis (PCA), a non-negative matrix factorization (NMF), a linear discriminant analysis (LDA), a generalized discriminant analysis (GDA), or a canonical correlation analysis (CCA). In another aspect, the method further comprises clustering the subjects into one or more groups based on at least one of the principal components. In another aspect, the method further comprises clustering the subjects into one or more phenotypes based on at least one of the principal components. In another aspect, the method further comprises characterizing the subjects and a disease process based on at least one of the principal components. In another aspect, the set of principal components explain a specified percentage of the high dimensional space. In another aspect, the method further comprises: determining an association between the set of principal components and one or more imaging, clinical and pathologic variables; and providing the association via the input/output interface. In another aspect, the method further comprises: receiving a medical data for a new subject via the input/output interface; analyzing the medical data based on the set of principal components using the one or more processors; and providing a diagnosis or a recommendation based on the analyzed medical data via the input/output device. In another aspect, the recommendation comprises a selection or exclusion of a therapy, medication, diagnostic testing, clinical trial or referral for the new subject. In another aspect, the method further comprises automatically predicting a post-mortem pathology for the new subject. In another aspect, the input/output interface comprises a remote device, and the remote device is communicably coupled to the one or more processors via one or more networks. In another aspect, the computing device comprises a server computer, a workstation computer, a laptop computer, a mobile communications device, a personal data assistant, or a medical device.

The present invention will now be described in reference to neurodegeneration related pattern formation in glucose uptake and machine learning.

At the core of the clinical practice of neurology is the localization of a particular clinical deficit to an anatomic substrate in the nervous system. For example, a lesion causing a focally weak limb can be localized to the muscle, neuromuscular junction, nerve, root, plexus, cord, brainstem, subcortex, or cortex. In neurodegenerative disorders of the brain, a patient's clinical symptoms manifest as selective impairments in mental abilities involved in sensation, perception, emotions, memory, social cognition, executive control, and/or behavior. Unfortunately, there is no functional-anatomic mapping of these brain functions at the macroscale to guide a targeted the clinical approach to these common conditions nor are there robust objective measures of brain functional organization used in clinical practice.

Neurodegenerative diseases produced characteristic large-scale patterns of alerted glucose uptake in the brain. Given the characteristic brain glucose uptake patterns produced by different neurodegenerative diseases, the Centers for Medicare and Medicaid Services (CMS) has determined that adequate evidence exists for the use of [F-18] fluorodeoxyglucose positron emission tomography (FDG-PET) in the evaluation of patients in the proper clinical context for differentiating Alzheimer's disease (AD) from frontotemporal dementia (FTD). FDG-PET is also a well established biomarker for AD and is included in the new research framework for AD [2]. FDG-PET has unique findings in dementia with Lewy bodies [3], normal pressure hydrocephalous [4,5], hippocampal sclerosis of aging and tau-negative amnestic dementia that clinically mimics AD in the elderly [6]. The wide applicability of FDG-PET in neurodegenerative diseases, based on variation of glucose uptake in brain regions that faithfully reflect the characteristic features of the clinical syndrome, implies that glucose uptake patterns contain information fundamental to neurodegenerative pathophysiology.

However, recent research indicates that brain glucose uptake patterns contain clinically relevant information for a diverse array of clinical situations beyond differentiating AD and FTD. These patterns are characterized by visual interpretations of raw and statistical results from semi-quantitative FDG-PET images. Specialized training in quantitative neuroimaging and behavioral neurology are required to optimize the clinical utility of these visual interpretations within the proper clinical context. In addition, standardized criteria for these clinical interpretations do not exist, complicating dissemination of expert knowledge in this area. This situation may be rectified through the use of modern big data analytics and machine learning (ML) technologies. The Mayo Clinic Alzheimer's Disease Research Center (ADRC) and the Mayo Clinic Study of Aging (MCSA) have developed a rich corpus of FDG-PET images with associated deep phenotyping (e.g., clinical, imaging, pathologic, genetic, etc.) making for an ideal environment to conduct a focused effort to develop a clinically meaningful ML application for brain FDG-PET images in the context of neurodegenerative diseases.

Two major limitations in modern ML algorithms, as commonly implemented in a medical context, revolve around developing labels for supervised learning and the lack of interpretability of the decision making used to predict outcomes. Unsupervised ML algorithms do not require labels, but it's difficult to properly define the feature set to be used and still may suffer from lack of interpretability. As previously described, the present invention provides a flexible unsupervised machine learning algorithm (i.e., does not require labels) for large scale patterns in FDG-PET that produces a highly interpretable synthesis of the learned information that has created new insights into the biology of AD. This algorithm uses a method referred to as Between-subject-variability Projection and Reduction (BPR) at its core. This technique produces a small number of images, or a basis set, that describe biologically relevant patterns that can be used to decode brain FDG-PET scans. Initial results in AD suggest that large-scale brain function can be described by a low-dimensional state space manifold, and all neurodegenerative disease alter flow across this manifold in some way. Therefore, this highly innovative ML algorithm has the potential to facilitate the creation of an FDG-PET decoder and classifier within a powerful biologically interpretable framework related to dementia biology.

These highly informative patterns are characterized by visual interpretations of raw and statistical results from semi-quantitative FDG-PET images. Specialized training in quantitative neuroimaging and behavioral neurology are required to optimize the clinical utility of these visual interpretations within the proper clinical context. In addition, standardized criteria for these clinical interpretations do not exist, complicating dissemination of expert knowledge in this area. This lack of objective and reproducible measures of key FDG-PET patterns has also produced a road block in designing convincing studies demonstrating the clinical utility of FDG-PET. This situation may be rectified through the use of modern big data analytics and machine learning (ML) technologies. The Mayo Clinic Alzheimer's Disease Research Center (ADRC) and the Mayo Clinic Study of Aging (MCSA) have developed a rich corpus of FDG-PET images with associated deep phenotyping (e.g., clinical, imaging, pathologic, genetic, etc.) making for an ideal environment to conduct a focused effort to develop a clinically meaningful ML application for brain FDG-PET images in the context of neurodegenerative diseases.

Having accurate and robust automatic brain FDG-PET scan readings will significantly improve the medical care provided to individuals suspected of having a neurodegenerative brain disease. An optimized automated FDG-PET decoder and interpretation algorithm will be used to introduce this technology into clinical practice.

The decoder is an optimized basis set for FDG-PET machine learning applications. The large corpus of FDG-PET data from the ADRC/MCSA studies are used to create the highest quality and widely applicable basis set for decoding FDG-PET images via the BPR procedure. This database includes normal aging, preclinical disease states, and all available data from age-associated neurodegenerative diseases. This will more completely sample the GFSS (theoretically cover the full color spectrum in FIGS. 18 and 19). The BPR algorithm is then optimized using: (1) prediction performance accuracy on parameters defining a nonlinear computational model of pattern formation; (2) original image reconstruction accuracy (see FIG. 16); (3) bootstrapped sampling stability; (4) longitudinal self-match accuracy; (5) meta-data predictive potential (see FIGS. 17); and (6) nearest neighbor clinical diagnostic similarity. The linear dimensionality reduction performance is compared to non-linear dimensionality reduction techniques. Supervised ML algorithms are explored for defining subspaces, including linear discriminant analysis, and compared these to the unsupervised performance.

The classifier is an algorithm for interpreting brain FDG-PETs in the context of suspected neurodegenerative dementia syndromes. A classification task specific labeling schema (e.g., control vs. MCI vs. dementia, neurodegenerative dementia phenotype, prediction modeling of clinical or pathologic outcomes) linking participants, used in creation of the FDG-PET decoder, is used to key meta-data. Unsupervised classification approaches linking new FDG-PET images to the labeled basis-set are developed using nearest-neighbor and exemplar-based matching in the state space manifold, or GFSS. These unsupervised results will be compared to supervised ML approaches with rigorous cross-validation. The ADNI database is utilized for external validation of the automated clinical interpretation algorithm with respect to CN, MCI, and Alzheimer's dementia. The predictive ability for clinical and pathologic outcomes are validated in ADNI (e.g., FIG. 17).

The robust automated FDG-PET decoder and interpretation algorithm (classifier) rely on highly interpretable and biologically meaningful decision making processes. The functional and phenotypic features of the state space described by the FDG-PET basis set are characterized. The images used in the FDG-PET encoder/decoder are used in a task-based functional MRI meta-analysis and to generate canonical functional brain networks (See FIG. 18 Panel B). The ability of the basis set to describe canonical functional brain networks derived from resting state functional MRI is tested. A latent variable analysis is performed on fMRI data and the relationship between those latent variables and the GFSS are examined. The functional mapping of this state space is compared to clinical phenotyping of neurodegenerative dementia syndromes.

Mental abilities emerge at a global level from local interactions across the brain. Neurodegenerative diseases cause a decline in mental abilities through disruption of this emergent global architecture. However, the neurobiology of mental abilities and neurodegenerative disease at the global scale is poorly understood. Neurodegenerative diseases alter mental abilities in a way that manifests in specific large-scale patterns of altered glucose uptake measured by FDG-PET. The approach described herein uses global patterns of glucose uptake as an observable feature of macroscale cognitive physiology during normal aging and in cognitively impaired individuals with neurodegenerative diseases. Variability in these patterns of glucose uptake encodes the macroscale consequence of physiology related to altered cognition, and the BPR algorithm parametrizes this variability in order to decode global cognitive physiology. BPR is a latent variable analysis. It is a higher-dimensional computational equivalent of the 2-D eigenfaces facial recognition algorithm as implemented by Turk and Pentland [7]. The algorithm derives a lower dimensional basis-set of 3-D eigenbrains or EBs. This technique allows characterization of fundamental axes of brain organization in patients with AD. The FDG-PET decoder produced from this analysis describes a low-dimensional state space manifold that characterizes broad categories of mental abilities affected by neurodegenerative diseases of the brain. This is referred to as the global functional state space (GFSS).

Figure 13:
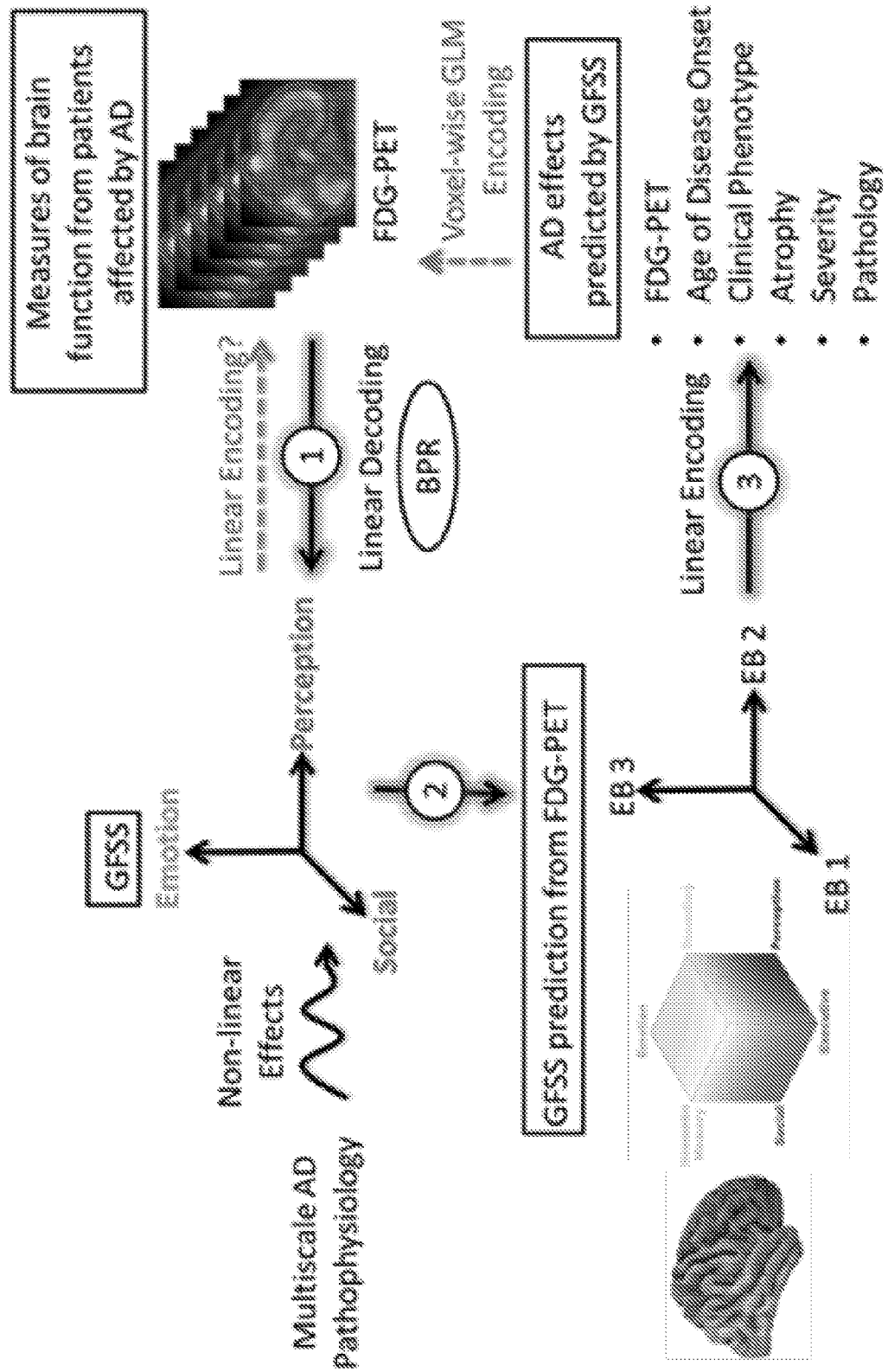
FIG. 13 is a graphical outline of this study in accordance with one embodiment of the present invention.

FIG. 13 is a graphical outline of this study in accordance with one embodiment of the present invention. Alzheimer's disease pathophysiology is assumed to involve complex non-linear dynamics related to the interaction between microscale and macroscale functional-anatomic organization of the brain needed to produce emergent cognitive abilities. These non-linear effects may perturb the emergent cognitive repertoire at the macroscale, or global functional state space (GFSS), in a heterogeneous fashion leading to individual variability in the expression of this pathophysiology at the macroscale. FDG-PET is a sensitive marker of the global pattern of neurodegenerative functional disruption at the individual level. Therefore, individual variability in global FDG-PET patterns can be considered an observable parameterization of macroscale functional AD pathophysiology. If the hypothesis that the GFSS is the underlying macroscale factor related to this disease expression, then a latent variable analysis of the observable variability in FDG-PET should produce a functional-anatomic mapping of the GFSS. This factor analysis assumes the underlying unseen variables are continuous and normally distributed. Therefore, the first part of this study performs a form of factor analysis computationally equivalent to the eigenface facial recognition algorithm, Between-subject variability Projection and Reduction (BPR), to identify spatially interpretable latent factors related to AD physiology. In the second part of this study, this newly identified GFSS is mapped onto functional connectivity and functional terminology. In the third part of this study, the GFSS is used to make predictions about other manifestations of AD pathophysiology. This allows for predictive modeling of key AD pathophysiologic manifestations.

The unsupervised machine learning algorithm, BPR, was designed to capture pathophysiologic information present in between-subject variability in a disease parameter of interest. This algorithm conceptualizes multivariate medical data from an individual as representing a particular parameterization of a (patho)physiological process of interest and uses individual differences in this parametrization to define a high dimensional space that contains a smaller dimensional subspace that describes global features of the disease state of interest. This lower dimensional subspace can be isolated in many ways, but ideally the dimensionality reduction technique used would retain interpretability in order to facilitate understanding of the pathophysiology of interest and be able to meaningfully place new subjects into the learned subspace and make predictions about clinical variables of interest.

For this study, it was assumed that macroscale glucose uptake patterns in cognitively impaired individuals with amyloid plaque deposits (N=423) represented a parameterization of macroscale AD pathophysiology. The between-subject variability of interest to this study was isolated from these preprocessed FDG-PET scans in the following way. The preprocessed FDG-PET images are three-dimensional arrays of voxel intensities that correspond to SUVR values in a standard template space. Taking only the voxel intensities that fall within the set of voxels, V, that have a greater than 15% probability of being gray matter in template space, this three-dimensional array can be reduced to a one-dimensional vector, $\Psi$, with 150,468 elements defined by V. To isolate subject effects, each element is non-parametrically standardized by the median, k, and interquartile range, $\tilde{Q}$, for that element across subjects $\Gamma_i=(\Psi_i-\tilde{X})\tilde{Q}^{-1}$ (see FIG. 2 for surface renderings of $\tilde{X}$ and $\tilde{Q}$). Let the set of these standardized vectors, with 150,468 elements per image, be $\Gamma_1$, $\Gamma_2$, $\beta_3$ ... $\Gamma_M$, where M is the number of participants studied (M=423). Subject-wise centering of each image is represented by the vector $$\Phi_i = \Gamma_i - \frac{1}{V}\sum_{n=1}^{V}\Gamma_i.$$

This can men De used to represent the individual differences of interest in the brain images between each image pair, or between subject variance, by calculating the subject-wise M by M matrix L, $$L=A^TA \quad (1)$$

where the matrix $A=[\Phi_1 \, \Phi_2 \, ... \, \Phi_M]$. This high-dimensional projection of individual differences can be represented as an eigen decomposition, using the singular-value decomposition $L=v\varepsilon v^T$, such that the M eigenvectors, $v_i$, of L, determine the linear combination of the M set of FDG-PET images that produce image space eigenvectors, $u_l$, or eigenbrains (EBs) given that they can be ordered into a three-dimensional configuration corresponding to the original brain images, as previously described for the eigenfaces facial recognition algorithm for two-dimensional facial recognition (6):

$$u_l = \sum_{k=1}^{M} v_{ik}\Phi_K \quad l = 1, ..., M \quad (2)$$

This was demonstrated while considering that the eigenvectors $v_i$ of $A^TA$ such that $$A^TAv_i=\mu_iv_i \quad (3)$$

multiplying both sides by A, $$AA^TAv_i=\mu_iAv_i \quad (4)$$

it is shown that $Av_i$ are the eigenvectors of the larger dimensional covariance matrix (150,468 by 150,468) in image space, $C=AA^T$. This algorithm demonstrates how individual differences in macroscale multivariate patterns in brain images can be mapped back into the original image space in the form of a compact lower-dimensional basis-set of eigenbrains (EBs). This allows for a highly interpretable understanding of the parameterization of a disease processes affecting the individuals included in the analysis.

Figure 14:
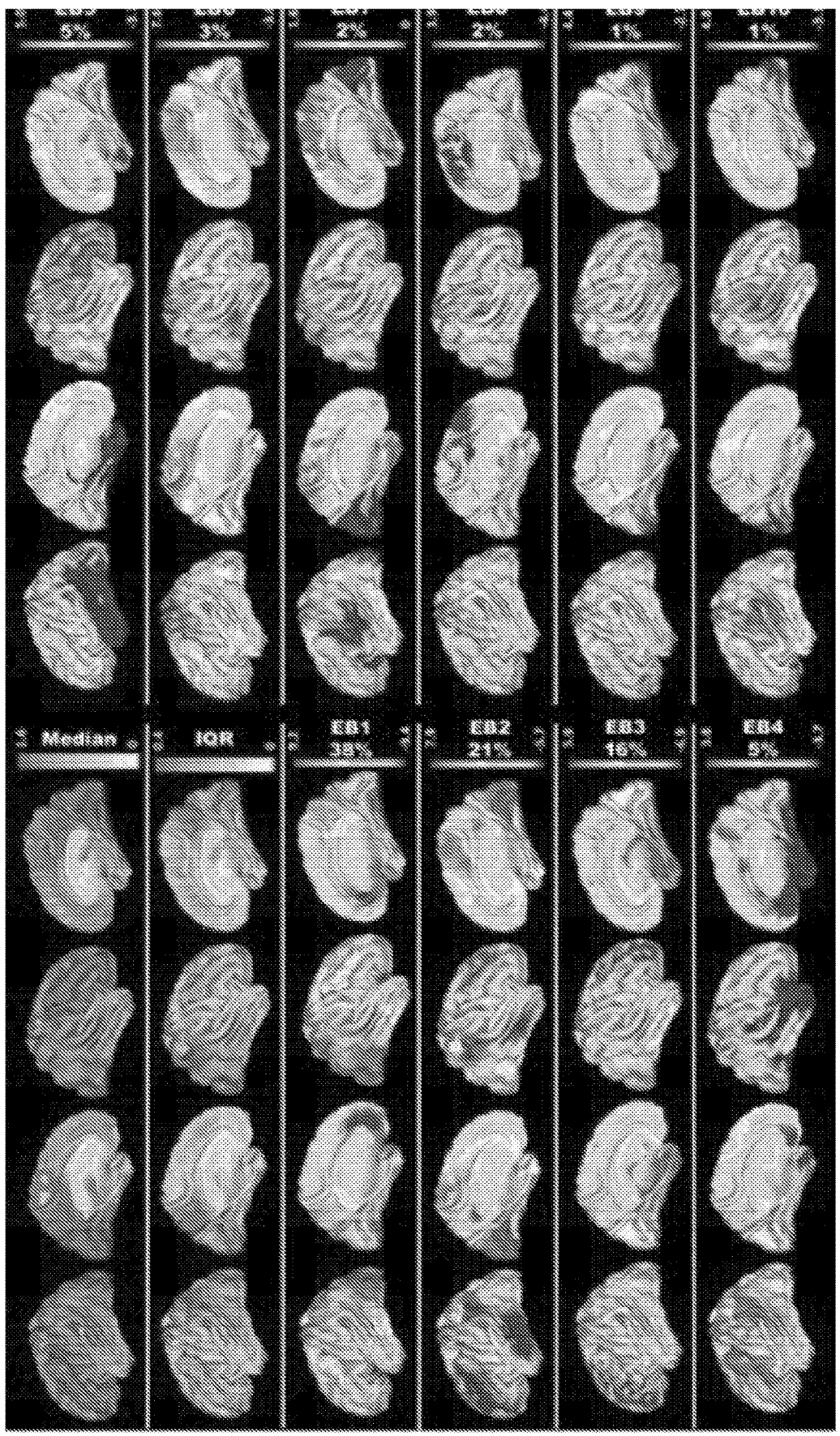
FIG. 14 depicts an Eigenbrain decomposition of FDG-PET in accordance with one embodiment of the present invention.

FIG. 14 depict Eigenbrain decomposition of FDG-PET in accordance with one embodiment of the present invention. Surface renderings of median, interquartile range, and EB intensities for the first 10 EBs. The percentage of variance explained by each is listed to the right of the color bar.

FIG. 15 is a graph showing the cumulative percentage of variance explained for the first 30 eigenbrains in accordance with one embodiment of the present invention. The first 10 eigenbrain explain 95% of the variance in this dataset.

Using only these 10 EBs, $u_i$, and the eigenvectors $v_i$, of L, as a subject-level weight, an individual FDG-PET scan can be estimated, $\Psi^{est}$, from a linear combination of EBs in following way:

$$\Psi^{est} = \tilde{X} + \sum_{i=1}^{n=10} v_i u_i \tilde{Q} \quad (5)$$

An example of an estimated image using only these 10 EBs relative to the original image is presented in FIG. 16. Using additional EBs adds additional structural information, but this does not appear relevant to quantifying dysfunction in the GFSS or enhance predicative ability (see below). FIG. 16 depicts an Eigenbrain based reconstruction of one subject in accordance with one embodiment of the present invention. In Panel A, the voxel intensities in the original FDG-PET scan from one subject are plotted versus the voxel intensities of the projected images reconstructed from a 10-EB model. Red dotted line is the line of identity. The solid white line is the least square fit of the data points. In Panel B, orthogonal slices of the original images (top), projected image (middle), and the difference image between the two overlaid on the gray matter segmentation (bottom). The regions in red in the difference image indicates regions that are present in the projected images but are not in the original image. These regions correspond to anatomic variations in the subject's gray matter and are not related to global metabolic patterns.

In order to determine the robustness of this algorithm to place an unseen image into this same GFSS mapping, the algorithm was iterated 422 times leaving out each subject exactly once and estimated the subject level weights, $v_i$, for the left out subject using the first 10 EBs, $u_i$, and the associated singular values, $\varepsilon_{i,i}$, derived from the remaining 422 subjects. These estimates were then compared to the derived values from the original run that included all 423 subjects. The set of subject-level weights, $v_i$, for an unseen image, $\Gamma_m$, for each of the 10 EBs, $u_i$, was calculated in the following way:

$$v_{i,m} = \frac{\sum_{i=1}^{n=10}\Gamma_m u_i}{\varepsilon_{i,i}} \quad (6)$$

The concordance between the original values and the estimated values was assessed using the absolute value, given that the sign is indeterminate and may change on a given iteration. We hope to address the sign indeterminacy problem as part of this propose project. The method demonstrated a robust performance with Kendall's coefficient of concordance approaching 1, indicating near complete agreement between the full model and the estimates obtained for the unseen left out subjects using equation [7] (data not shown). To assess the sample-related bias of the basis-set produced by this data-set, we generated 500 bootstrapped samples were generated and the first 10 EBs per sample were calculated and compared the correlation of the absolute values of the EB images produced to the EBs from the original model. All 10 EBs appeared to be robust to sample variation with relatively more variation seen in the EBs explaining less than 5% of the variance in the original data (data not shown).

To evaluate the out-of-sample predictive ability of the GFSS for key measures of the effects of AD pathophysiology (i.e., age, glucose uptake, cognition, and disease severity), the publically available multisite data from the Alzheimer's Disease Neuroimaging Initiative (ADNI) database (adni.loni.usc.edu) was used. The data from 410 ADNI subjects was analyzed with FDG-PET scans, CDR greater than 0, and positive amyloid PET imaging as defined by previously established ADNI cut-point (1.11 for whole cerebellum referenced AV45 data).

Figure 17:
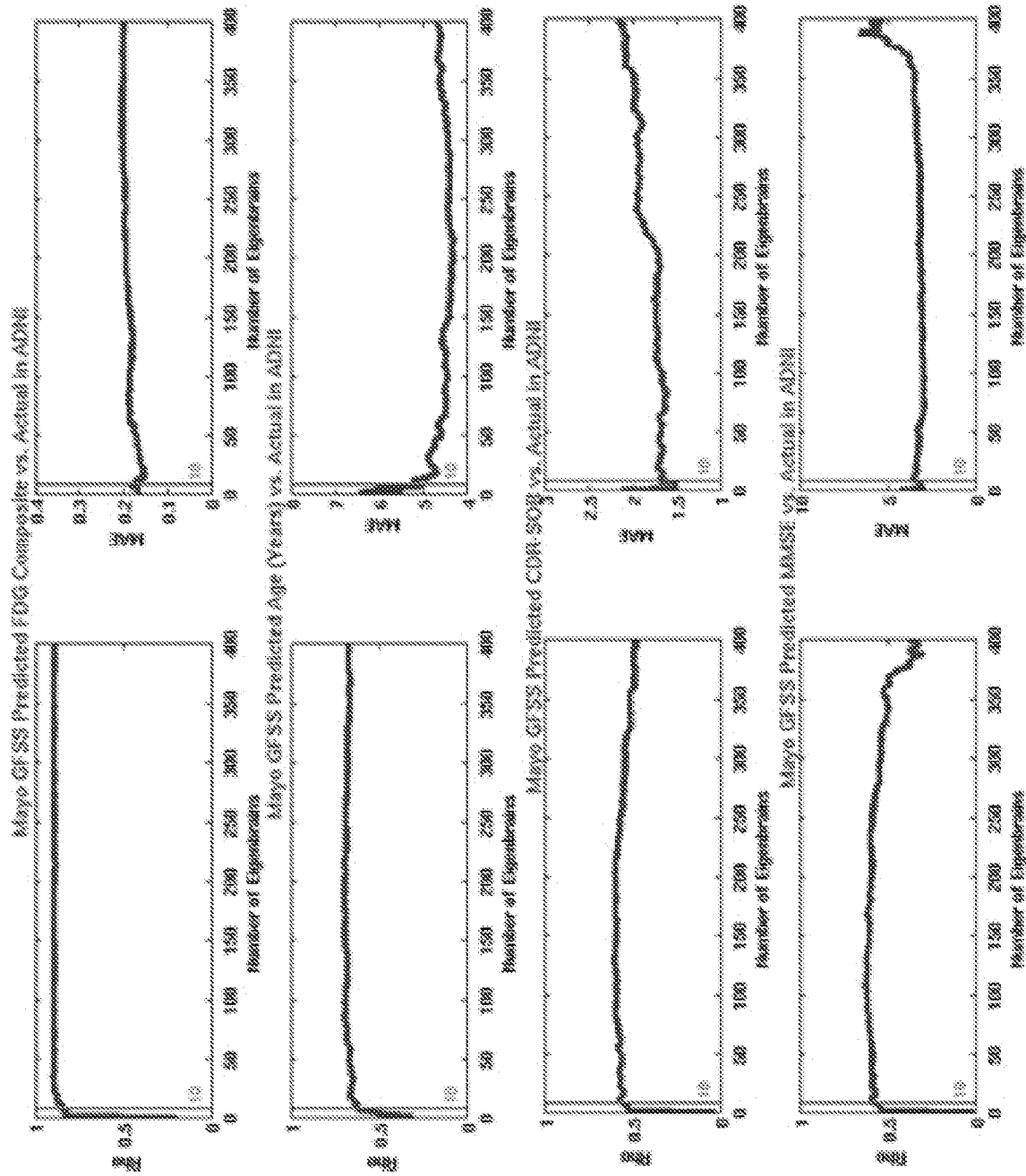
FIG. 17 shows the effect of model order on global functional state space predictive modeling of FDG, age, severity, and cognition in ADNI in accordance with one embodiment of the present invention.

In this dataset, the FDG composite summary used in ADNI to summarize AD-like patterns of hypometabolism is not associated with age. However, once the eigenvalues for each of the first 10 EBs are calculated from an individual's FDG scan, the GFSS model fits in the Mayo data can be used to accurately predict the age of an individual and the FDG composite score (FIG. 5). The predictive ability of the GFSS models in the ADNI data is not substantially improved with additional EBs being included in the models for FDG composite, age, disease severity, or cognition as shown in FIG. 17. Comparisons were then performed between the GFSS, resting state functional connectivity, and task-based fMRI in order to better understand the biological underpinnings of this strong predictive ability.

FIG. 17 shows the effect of model order on global functional state space predictive modeling of FDG, age, severity, and cognition in ADNI in accordance with one embodiment of the present invention. The Pearson correlation coefficients between the actual and predicted values are plotted versus the number of eigenbrains used in the predictive model for each of the variables (left). The mean absolute error (MAE) of the prediction is plotted versus the number of eigenbrains used in the predictive model for each of the variables (right). The near optimal performance of the 10-D model is highlighted by the red vertical bar in each plot.

Figure 18:
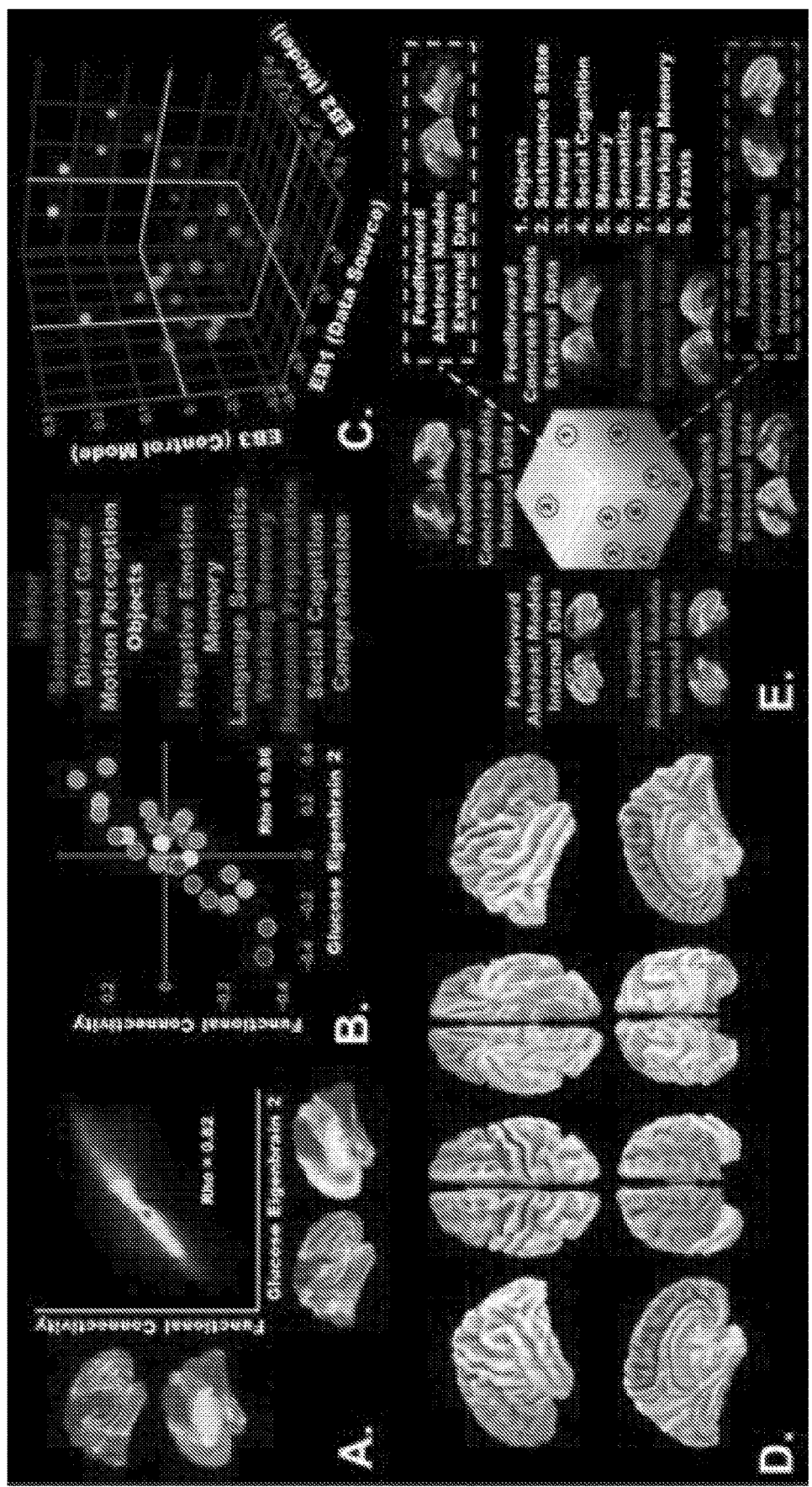
FIG. 18 depicts the functional-anatomic organization of the global functional state space in accordance with one embodiment of the present invention.

In this cohort, the first three EBs account for 75% of the variance and are related to symmetric orthogonal axes of brain function that capture the majority of the hypothetical GFSS. FIG. 18 depicts the functional-anatomic organization of the global functional state space in accordance with one embodiment of the present invention. Panel A depicts the principle gradient of macroscale functional cortical organization versus EB2. Panel B depicts the neurosynth decoding of functional connectivity versus EB2 decoding. Select topic terms sampling the range of EB2 and are color-coded to right. The color coding is based on the scatter plot in panel C. Panel C depicts the three-dimensional plot with the Neurosynth decoding of EB1-3. For the color-coding, each EB decoding was used as a channel in a RGB color scheme (EB1=Blue, inverted polarity EB2=Red, EB3=Green). The radius of the points encodes depth along EB2. Panel D depicts the same RGB color-coding was applied in a voxel-wise manner using the intensities from EB1-3 and is displayed on a rendering of the entire brain. Panel E depicts the state space representation of the same color mapping with the approximate location of nine cognitive topic terms from panel C overlaid and numbered. A surface rendering of the anatomic correlates, generated from linear combinations of EB1-3 weighted by the position in state space, for the eight extremes of the cube are displayed near the portion of state space represented A nearly identical functional axis as was captured in EB2 has recently been described [8] using functional connectivity data from cognitively unimpaired individuals (FIG. 18 Panels A and B). This suggests that global variation in glucose metabolism in AD takes place along macroscale functional network gradients, and supports our hypothesis that AD alters flow through a global functional manifold [9] that describes large-scale network configurations that support cognition [10,11]. A NeuroSynth (www.neurosynth.org) functional topic terms based decoding facilitated a mapping between these orthogonal anatomic spatial gradients and functional terminology (FIG. 18 Panels C and D). This structural-functional mapping can be represented in a three-dimensional approximation of the GFSS. Each axis, or latent variable, can be conceptually simplified and dichotomized via axis polarity based on this mapping (data source [internal/external], model form [abstract/concrete], and control type [feedback/feedforward] for EB1-3 respectively).

Figure 19:
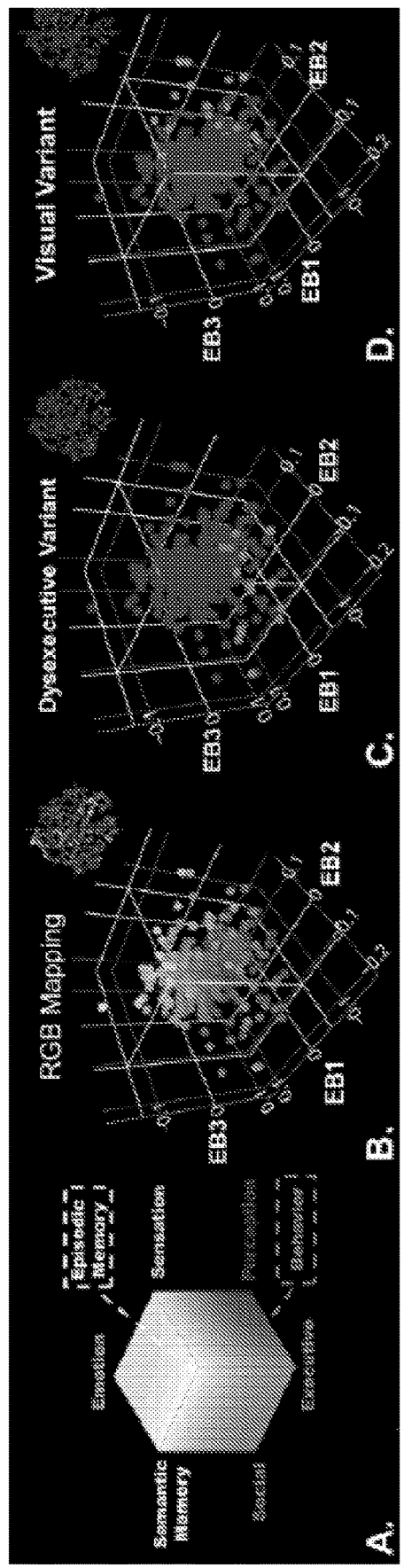
FIG. 19 depicts glucose patterns from patients projected into global functional state space in accordance with one embodiment of the present invention.

In order to visualize how decoded FDG images from individual subjects relate to the GFSS coordinates, the eigenvalues of each individual subject was projected onto a 3-D GFSS mapping as depicted in FIG. 19 in accordance with one embodiment of the present invention. In Panel A, the GFSS color mapping defined in FIG. 18 is displayed for reference with conceptual labels used to describe impaired mental abilities in clinical syndromes. Subject weights for EB1-3 are plotted in a 3-D with a 2-D UMAP projection of the full 10-D EB manifold inset. In Panel B, the same color coding scheme as was used in FIG. 18, is used here for individual participants. In Panel C, patients with the dysexecutive variant of AD dementia are highlighted. In Panel D, patients with the visual variant of AD dementia are highlighted.

The majority of the glucose uptake changes captured by the decoding centered on the area of the GFSS which maps onto parietal and temporal association cortex related to episodic memory encoding and retrieval. Individuals that mapped more distantly from this area showed abnormalities in portions of the GFSS associated with social, executive, or visual processing regions. These eccentrically located individuals tended to be younger and identified by clinicians as having atypical clinical phenotypes matching the functions predicted by the GFSS mapping. Patients with FTD would likely be projected to the opposite portion of the state space associated with behavior, but given that these subjects were not included in the development of the basis set, this is uncertain.

Figure 20:
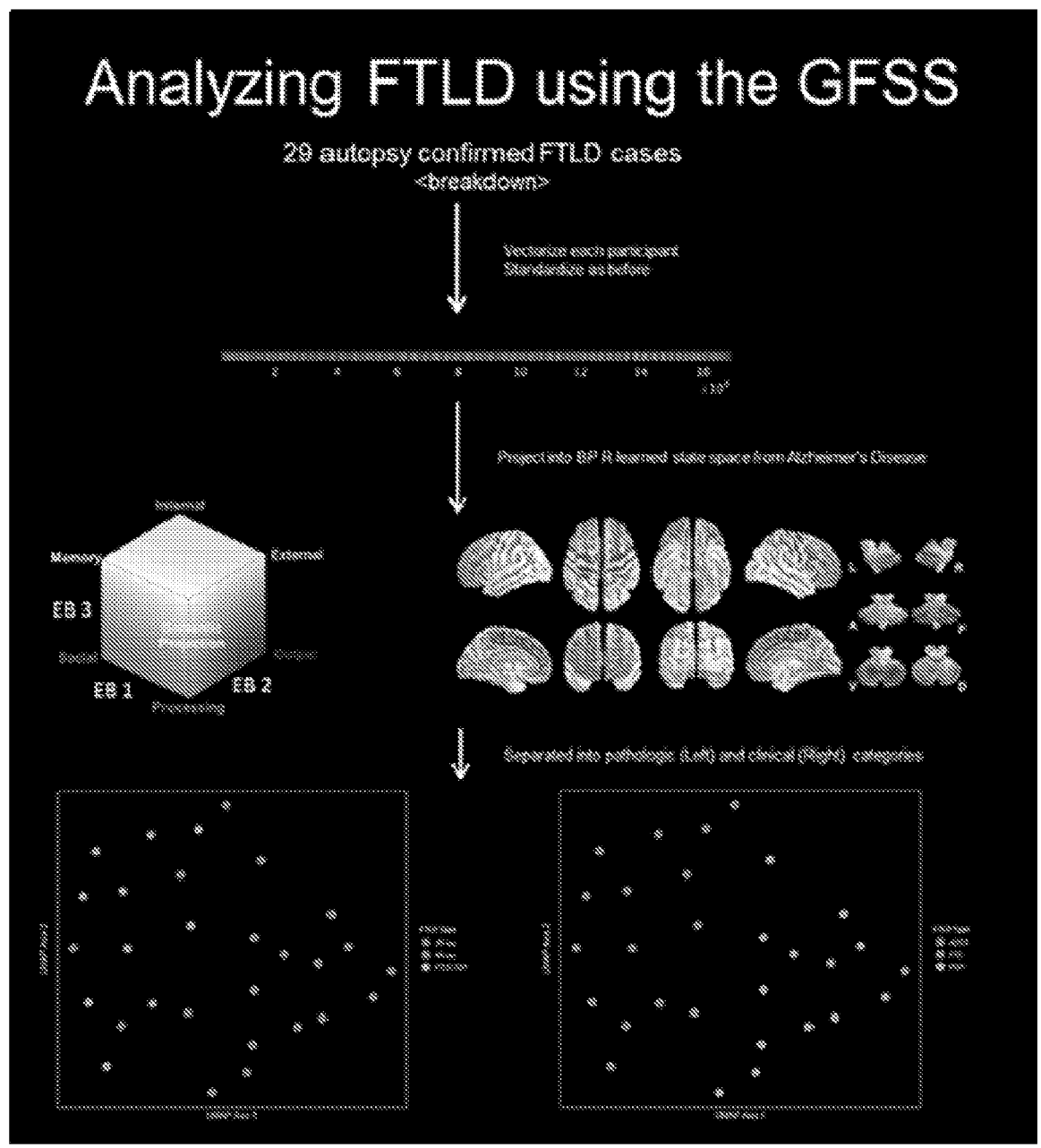
FIG. 20 depicts a process for analyzing FTLD using the GFSS in accordance with one embodiment of the present invention.

FIG. 20 depicts a process for analyzing FTLD using the GFSS in accordance with one embodiment of the present invention. Twenty-nine autopsy confirmed FTLD cases were used. The data for each participant is vectorized and standardized as previously described. Thereafter, the data is projected into the BPR learned state space from AD, and separated into pathologic (left bottom panel) and clinical (right bottom panel) categories.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Lowe V, Senjem M, Lund E, Jones D, Weigand S, Knopman D, Boeve B, Kantarci K, Petersen R, Schwarz C, Jack C. Variability of PiB accumulation in white matter. HAI (2016) Miami (P0101).
2. C. R. Jack, Jr. et al., NIA-AA Research Framework: Toward a biological definition of Alzheimer's disease. Alzheimers Dement 14, 535-562 (2018).
3. J. Graff-Radford et al., Dementia with Lewy bodies: basis of cingulate island sign. Neurology 83, 801-809 (2014).
4. R. A. Townley et al., (18)F-FDG PET-CT pattern in idiopathic normal pressure hydrocephalus. Neuroimage Clin 18, 897-902 (2018).
5. N. R. Graff-Radford, D. T. Jones, Normal Pressure Hydrocephalus. Continuum (Minneap Minn) 25, 165-186 (2019).
6. H. Botha et al., FDG-PET in tau-negative amnestic dementia resembles that of autopsy-proven hippocampal sclerosis. Brain 141, 1201-1217 (2018).
7. M. Turk, A. Pentland, Eigenfaces for recognition. J Cogn Neurosci 3, 71-86 (1991).
8. D. S. Margulies et al., Situating the default-mode network along a principal gradient of macroscale cortical organization. Proc Natl Acad Sci USA 113, 12574-12579 (2016).
9. J. M. Shine et al., Human cognition involves the dynamic integration of neural activity and neuromodulatory systems. Nat Neurosci 22, 289-296 (2019).
10. D. T. Jones et al., Tau, amyloid, and cascading network failure across the Alzheimer's disease spectrum. Cortex 97, 143-159 (2017).
11. D. T. Jones et al., Cascading network failure across the Alzheimer's disease spectrum. Brain 139, 547-562 (2016).

What is claimed is:

1. A computerized method for determining a set of principal components in a multivariate medical data corresponding to a group of subjects comprising:
   providing a computing device comprising an input/output interface, a memory and one or more processors communicably coupled to the input/output interface and the memory;
   receiving the multivariate medical data corresponding to the group of subjects via the input/output interface or the memory, wherein the multivariate data includes imaging data;

identifying a set of variables based on metabolic patterns in the multivariate medical data between the subjects in the group using the one or more processors by:
three-dimensional standard space ordering of FDG-PET voxels in the imaging data,
creating a mask by one-dimensional ordering of the FDG-PET voxels that are in gray matter voxels,
voxel-wise standardization of the FDG-PET voxels across all subjects in the group using the mask, and
identifying one or more of the set of variables using the voxel-wise standardization of the FDG-PET voxels;
representing the multivariate medical data corresponding to the set of variables in a high dimensional space between the subjects in the group using the one or more processors;
determining the set of principal components by reducing the high dimensional space between the subjects in the group to a compact representational space using the one or more processors; and
providing the set of principal components via the input/output interfaces;
receiving a medical data for a new subject via the input/output interface;
analyzing the medical data based on the set of principal components using the one or more processors; and
providing a diagnosis or a recommendation based on the analyzed medical data via the input/output device, wherein the recommendation comprises a selection or exclusion of a therapy, medication, diagnostic testing, clinical trial or referral for the new subject.

2. The method of claim 1, further comprising selecting the multivariate medical data for the group of subjects based on one or more medical observations.

3. The method of claim 1, wherein the multivariate medical data comprises an image data, a clinical test result, an individual characteristic or a combination thereof for each of the subjects.

4. The method of claim 1, further comprising pre-processing the multivariate data.

5. The method of claim 1, wherein determining the set of principal components by reducing the high dimensional space between the subjects to a compact representational space is performed using a principal component analysis (PCA), a non-negative matrix factorization (NMF), a linear discriminant analysis (LDA), a generalized discriminant analysis (GDA), or a canonical correlation analysis (CCA).

6. The method of claim 1, further comprising clustering the subjects into one or more groups based on at least one of the principal components.

7. The method of claim 1, further comprising clustering the subjects into one or more phenotypes based on at least one of the principal components.

8. The method of claim 1, further comprising characterizing the subjects and a disease process based on at least one of the principal components.

9. The method of claim 1, wherein the set of principal components explain a specified percentage of the high dimensional space.

10. The method of claim 1, further comprising:
determining an association between the set of principal components and one or more imaging, clinical and pathologic variables; and
providing the association via the input/output interface.

11. The method of claim 1, further comprising automatically predicting a post-mortem pathology for the new subject.

12. An apparatus for determining a set of principal components in a multivariate medical data corresponding to a group of subjects comprising:
an input/output interface;
a memory;
one or more processors communicably coupled to the input/output interface and the memory, wherein the one or more processors receive the multivariate medical data corresponding to the group of subjects via the input/output interface or the memory wherein the multivariate data includes imaging data, identify a set of variables based on metabolic patterns in the multivariate data between the subjects in the group, represent the multivariate medical data corresponding to the set of variables in a high dimensional space between the subjects in the group, determine the set of principal components by reducing the high dimensional space between the subjects in the group to a compact representational space, provide the set of principal components via the input/output interfaces, receive a medical data for a new subject via the input/output interface, analyze the medical data based on the set of principal components using the one or more processors, and provide a diagnosis or a recommendation based on the analyzed medical data via the input/output device, wherein the recommendation comprises a selection or exclusion of a therapy, medication, diagnostic testing, clinical trial or referral for the new subject; and
wherein the one or more processors identify the set of variables based on metabolic patterns in the multivariate medical data between the subjects in the group by: three-dimensional standard space ordering of FDG-PET voxels in the imaging data, creating a mask by one-dimensional ordering of the FDG-PET voxels that are in gray matter voxels, voxel-wise standardization of the FDG-PET voxels across all subjects in the group using the mask, and identifying one or more of the set of variables using the voxel-wise standardization of the FDG-PET voxels.

13. The apparatus of claim 1, wherein the one or more processors automatically predict a post-mortem pathology for the new subject.

14. The apparatus of claim 12, wherein the input/output interface comprises a remote device, and the remote device is communicably coupled to the one or more processors via one or more networks.

15. The apparatus of claim 12, wherein the computing device comprises a server computer, a workstation computer, a laptop computer, a mobile communications device, a personal data assistant, or a medical device.

16. The apparatus of claim 12, wherein determining the set of principal components by reducing the high dimensional space between the subjects to a compact representational space is performed using a principal component analysis (PCA), a non-negative matrix factorization (NMF), a linear discriminant analysis (LDA), a generalized discriminant analysis (GDA), or a canonical correlation analysis (CCA).

17. The apparatus of claim 12, wherein the one or more processors cluster the subjects into one or more groups or phenotypes based on at least one of the principal components.

18. The apparatus of claim 12, wherein the one or more processors characterize the subjects and a disease process based on at least one of the principal components.

19. The apparatus of claim 12, wherein the set of principal components explain a specified percentage of the high dimensional space.

20. The apparatus of claim 12, wherein the one or more processors:
- determine an association between the set of principal components and one or more imaging, clinical and pathologic variables; and
- provide the association via the input/output interface.

* * * * *